(12) United States Patent
Turturro et al.

(10) Patent No.: US 10,842,583 B2
(45) Date of Patent: *Nov. 24, 2020

(54) MEDICAL KIT AND ASSOCIATED SYSTEMS AND METHODS FOR PREVENTING CENTRAL LINE ASSOCIATED BLOOD STREAM INFECTION

(71) Applicant: Medline Industries, Inc., Northfield, IL (US)

(72) Inventors: Michael Turturro, Arlington Heights, IL (US); Mike Stankiewicz, Chicago, IL (US); Barbara Connell, Lake in the Hills, IL (US); Mika Hulliberger, Chicago, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/833,551

(22) Filed: Mar. 28, 2020

(65) Prior Publication Data

US 2020/0222140 A1 Jul. 16, 2020

Related U.S. Application Data

(63) Continuation of application No. 15/492,864, filed on Apr. 20, 2017, now Pat. No. 10,639,120, which is a
(Continued)

(51) Int. Cl.
*A61B 50/30* (2016.01)
*A61B 46/10* (2016.01)
(Continued)

(52) U.S. Cl.
CPC .............. *A61B 50/30* (2016.02); *A61B 46/10* (2016.02); *B65D 65/02* (2013.01);
(Continued)

(58) Field of Classification Search
CPC ......... A61B 50/30; A61B 46/10; A61B 46/00; A61B 2050/002; A61B 2050/3008;
(Continued)

(56) References Cited

U.S. PATENT DOCUMENTS 3,329,261 A 7/1967 Serany, Jr. et al.
3,503,391 A 3/1970 Melges
(Continued)

OTHER PUBLICATIONS

"AllPoints Dressing Change Systems", AllPoints Dressing Change Systems; Bard Access Systems; bard access.com/AllPoints-dressing-change-systems; Published in 2015.
(Continued)

*Primary Examiner* — Steven A. Reynolds
(74) *Attorney, Agent, or Firm* — Philip H. Burrus, IV

(57) ABSTRACT

A medical kit 100 includes a drape 1323. A plurality of pockets (1302,1303,1304,1305, 1306,1307) are disposed along a bottom edge of the drape 1323 in a linear, side-by-side arrangement. A plurality of medical implements (1310, 1311,1312,1313,1314,1315) are stowed in the plurality of pockets on a one-to-one basis. Medical indicia (1316,1317, 1318,1319,1320,1321) is disposed along each pocket. The medical indicia can include comprising one or more educational prompts that instruct medical personnel how to use a particular medical implement disposed in a pocket to complete a central catheter dressing change.

20 Claims, 20 Drawing Sheets

Related U.S. Application Data continuation-in-part of application No. 15/207,111, filed on Jul. 11, 2016, which is a continuation-in-part of application No. 15/131,839, filed on Apr. 18, 2016.

(51) Int. Cl.
    *B65D 65/02*     (2006.01)
    *B65D 75/58*     (2006.01)
    *A61B 50/00*     (2016.01)

(52) U.S. Cl.
CPC .... *B65D 75/5827* (2013.01); *A61B 2050/002* (2016.02); *A61B 2050/3008* (2016.02); *A61B 2050/314* (2016.02)

(58) Field of Classification Search
CPC ... A61B 2050/314; A61F 17/00; B65D 65/02; B65D 75/5827
USPC .................................. 206/570, 571, 572
See application file for complete search history.

(56) References Cited

U.S. PATENT DOCUMENTS

| | | | |
|---|---|---|---|
| 3,749,233 | A | 7/1973 | McCormick, Jr. |
| 3,791,382 | A | 2/1974 | Collins |
| 4,051,845 | A | 10/1977 | Collins |
| 4,342,390 | A | 8/1982 | Mitchell et al. |
| 4,457,026 | A | 7/1984 | Morris |
| 4,476,860 | A | 10/1984 | Collins et al. |
| 4,570,628 | A | 2/1986 | Neal |
| 4,573,576 | A | 3/1986 | Krol |
| 4,579,628 | A | 4/1986 | Renard et al. |
| 4,844,259 | A | 7/1989 | Glowczewskie, Jr. et al. |
| 5,335,373 | A | 8/1994 | Dresdner, Jr. et al. |
| 5,804,512 | A | 9/1998 | Lickfield et al. |
| 5,931,303 | A | 8/1999 | Salvadori |
| 6,579,271 | B1 | 6/2003 | Aruffo et al. |
| 7,293,654 | B1 | 11/2007 | Wilson et al. |
| 7,673,754 | B2 | 3/2010 | Wilson, Jr. et al. |
| 8,371,448 | B1 | 2/2013 | Reaux |
| 2005/0158510 | A1 | 7/2005 | Trump |
| 2008/0283426 | A1 | 11/2008 | Primer et al. |
| 2008/0283433 | A1 | 11/2008 | Primer |
| 2010/0274205 | A1 | 10/2010 | Morelli et al. |
| 2011/0041995 | A1 | 2/2011 | Adams |
| 2011/0290260 | A1 | 12/2011 | Tomes |
| 2012/0145589 | A1 | 6/2012 | Macinnes et al. |
| 2013/0152946 | A1 | 6/2013 | Sosnowski |
| 2015/0027922 | A1* | 1/2015 | Fresco .................. A61F 17/00 206/570 |
| 2015/0034521 | A1* | 2/2015 | Lien ...................... B65B 11/58 206/494 |
| 2015/0101616 | A1 | 4/2015 | Wiley et al. |
| 2015/0367011 | A1* | 12/2015 | Kalmon ................ A61B 50/30 428/12 |
| 2017/0368302 | A1* | 12/2017 | Brooks ................ A61M 25/02 |

OTHER PUBLICATIONS

"Appeal Decision", U.S. Appl. No. 15/131,839, filed Apr. 18, 2016; dated Aug. 30, 2019.
Han, Inho , "PCT Search Report and Written Opinion", PCT Application No. PCT/US2018/026279; Filed Apr. 5, 2018; dated Aug. 1, 2018.
Reynolds, Steven , "Final OA", U.S. Appl. No. 15/131,839, filed Apr. 18, 2016; dated Nov. 20, 2017.
Reynolds, Steven , "Final OA", U.S. Appl. No. 15/207,111, filed Jul. 11, 2016; dated Nov. 20, 2017.
Reynolds, Steven , "NonFinal OA", U.S. Appl. No. 15/131,839, filed Apr. 18, 2016; dated Oct. 31, 2016.
Reynolds, Steven , "NonFinal OA", U.S. Appl. No. 15/207,111, filed Jul. 11, 2016; dated Jul. 3, 2017.
Reynolds, Steven , "NonFinal Office Action", U.S. Appl. No. 15/131,839, filed Apr. 18, 2016; dated Jan. 3, 2020.
Reynolds, Steven , "NonFinal Office Action", U.S. Appl. No. 15/207,111, filed Jul. 11, 2016; dated Jan. 15, 2020.
Reynolds, Steven , "NonFinal Office Action", U.S. Appl. No. 15/207,111, filed Jul. 11, 2016; dated Oct. 31, 2016.
Reynolds, Steven A. , "Appeal Decision", U.S. Appl. No. 15/131,839, filed Apr. 18, 2016; dated Aug. 30, 2019.
Reynolds, Steven A. , "Appeal Decision", U.S. Appl. No. 15/207,111, filed Jul. 11, 2016; dated Aug. 30, 2019.
Reynolds, Steven A. , "Final Office Action", U.S. Appl. No. 15/131,839, filed Apr. 18, 2016; dated Feb. 27, 2017.
Reynolds, Steven A. , "Final Office Action", U.S. Appl. No. 15/207,111, filed Jul. 11, 2016; dated Feb. 24, 2017.
Reynolds, Steven A. , "Final Office Action", U.S. Appl. No. 15/492,864, filed Apr. 20, 2017; dated Sep. 12, 2018.
Reynolds, Steven A. , "NonFinal OA", U.S. Appl. No. 15/429,864, filed Apr. 20, 2017; dated Mar. 29, 2018.
Reynolds, Steven A. , "Notice of Allowance", U.S. Appl. No. 15/492,864, filed Apr. 20, 2017; dated Jan. 21, 2020.
Reynolds, Steven Alan , "NonFinal OA", U.S. Appl. No. 15/492,864, filed Apr. 20, 2017; dated Oct. 5, 2017.
Reynolds, Steven Alan , "Final Office Action", U.S. Appl. No. 15/131,839, filed Apr. 18, 2016; dated Apr. 27, 2020.

* cited by examiner

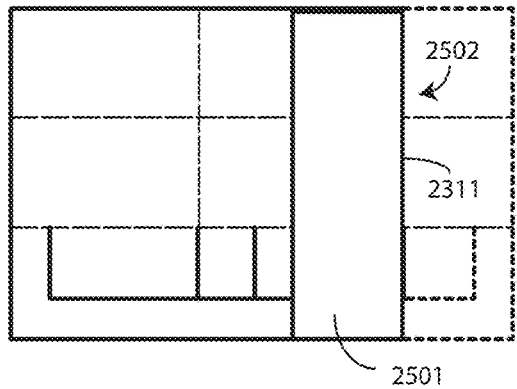
*FIG. 25*
*FIG. 26*
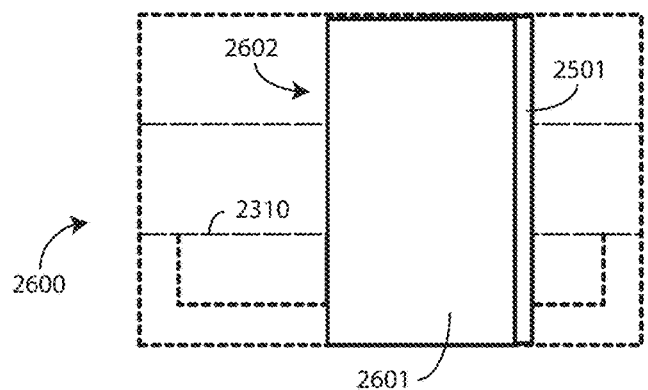
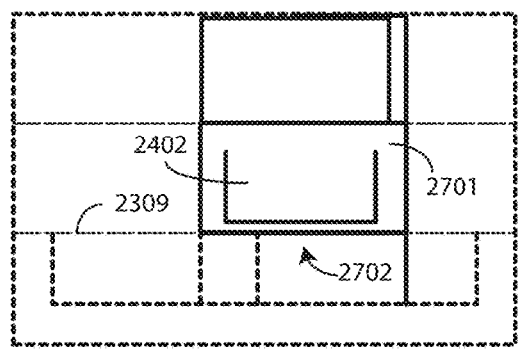
*FIG. 27*
*FIG. 28*
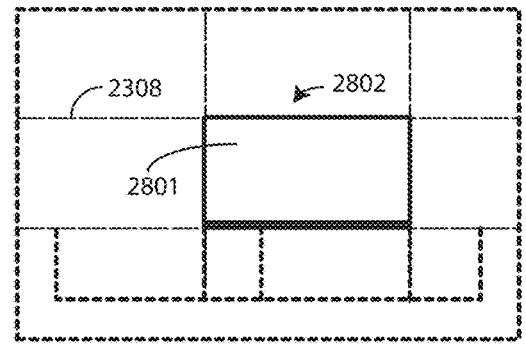

US 10,842,583 B2

MEDICAL KIT AND ASSOCIATED SYSTEMS AND METHODS FOR PREVENTING CENTRAL LINE ASSOCIATED BLOOD STREAM INFECTION

CROSS REFERENCE TO PRIOR APPLICATIONS

This application is a continuation of U.S. application Ser. No. 15,492,864, filed Apr. 20, 2017, which is a continuation-in-part of U.S. application Ser. No. 15/207,111, filed Jul. 11, 2016, which is a continuation-in-part of U.S. application Ser. No. 15/131,839, filed Apr. 18, 2016, each of which is incorporated by reference for all purposes.

BACKGROUND

Technical Field

This invention relates generally to medical kits, and more particularly to medical kits configured to facilitate prevention of infection and other complications during medical procedures.

Background Art

Healthcare facilities are increasingly concerned about the occurrence of secondary complications occurring during medical and surgical procedures. For example, during a medical procedure on an otherwise healthy patient, such as the insertion of an intravenous catheter, there is the possibility that a secondary infection or other complication can result. This problem is so significant, it has been named with the acronym "CLABSI," which stands for Central Line Associated Blood Stream Infection. CLABSI primarily occurs at one or more of three events: Catheter insertion, access line attachment to the catheter, and maintenance of the access line. As a result of the problems associated with CLABSI, more attention is being turned to establishment and maintenance of sterile fields about patients and procedure sites during medical procedures. It would be advantageous to have improved medical kits and associated methods and systems that help to prevent CLABSI.

BRIEF DESCRIPTION OF THE DRAWINGS

FIGS. 25-28 illustrate folding steps for one explanatory drape configured in accordance with one or more embodiments of the disclosure.

Figure 1:
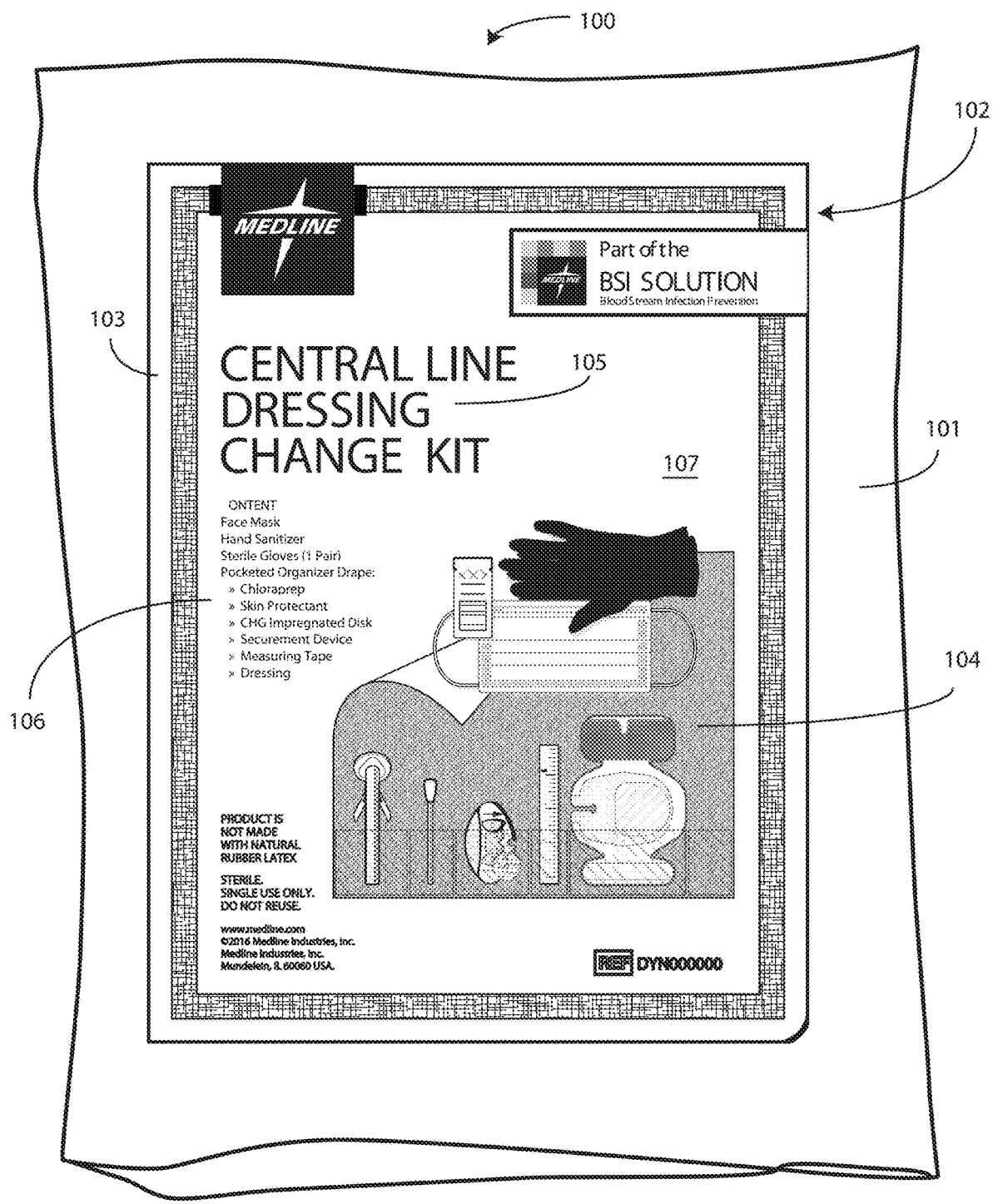
FIG. 1 illustrates one explanatory medical kit configured in accordance with one or more embodiments of the disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the disclosure are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." The terms "substantially" and "about" are used to refer to dimensions, orientations, or alignments inclusive of manufacturing tolerances. Thus, a "substantially orthogonal" angle with a manufacturing tolerance of plus or minus two degrees would include all angles between 88 and 92, inclusive. Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

A central catheter is a catheter that is placed into a large vein through which medical professionals may deliver fluids, dyes, or medications to a patient. For example, during angiogram procedures, medical professionals will insert a central catheter into an artery or vein. The catheter is then directed to the proper area within the patient. A special dye is then injected into the vessel so that the circulatory system will be visible to a radiographic camera.

Central catheters can also be used to withdraw fluids, such as blood, for testing. Central catheters can also be placed into a patient to allow prolonged intravenous access, such as for extended antibiotic treatment, chemotherapy, and so forth. In the former case, insertion is temporary. In the latter, central catheters can be left in place in the patient's arm for periods ranging from six weeks to one year.

Central catheters can be inserted into various parts of the patient. Frequently, they are inserted into the chest of a patient. Placement into vessels in the chest can be advantageous in some procedures in that the path through which the catheter must be guided is shorter from the chest to the heart than from another portion of the patient's body. Central catheters can be placed in other locations as well, however. For example, during angiograms catheters can be inserted into a blood vessel near the groin, such as the femoral artery or vein. They can also be placed into vessels in the arm. Central catheters inserted into arms are generally known as "peripherally" inserted central catheters.

Catheter insertion procedures are generally performed bedside or in a diagnostic lab room by a medical professional who specializes in catheter insertion. The medical professional is frequently a specially trained nurse. One exception to bedside insertion occurs during radiology procedures, such as angiograms, where the catheter is guided and inserted by a doctor.

Regardless of who inserts the catheter, or where it is inserted, bloodstream infection is continually a concern. It will be readily understood that insertion of a foreign object, which can be on a semi-permanent basis, into a patient's vein has associated therewith a risk that bacteria or other microbes will be introduced into the bloodstream during central catheter and peripherally inserted central catheter insertion procedures. Studies have shown that such infections can be a source of death.

While the largest percentage of these infections occurs at the time of catheter insertion, significant amounts of infection can occur when the insertion site is being cleaned and maintained. To combat this, some health care providers have begun to issue catheter insertion and maintenance procedure requirements that are similar to those used in surgery. For example, a catheter insertion or maintenance specialist may have to don hair covering, a mask, gloves, foot coverings, and a full-body sterile surgical gown, just as if they were entering an operating room. Such procedures also require the patient to be covered by a conventional medical drape. Such procedures attempt to ensure that a maximum barrier environment is established prior to the insertion of, and during the maintenance, use, or cleaning of, central catheter lines.

While the procedures are beneficial, they are insufficient for preventing bloodstream infections during central line procedures for two reasons: First, it is frequently the case that medical personnel performing line placement or maintenance operations are unfamiliar with "surgical" practices and aseptic techniques used during operations. Said differently, personnel working with central catheter devices generally do not work in the operating room, and are therefore frequently unacquainted with operating room procedures. Accordingly, such personnel therefore frequently lack understanding of certain techniques, including sterile field maintenance and other aseptic techniques. These deficiencies can cause breaks in aseptic techniques, thereby leading to an increased likelihood of infection.

Embodiments of the present invention work to solve both problems by providing an intuitive medical kit that assists medical personnel in executing method steps to clean central catheter insertion sites, replace dressings, and otherwise maintain a central catheter installation while adhering to proper aseptic techniques that minimize the likelihood of infection. Embodiments of the disclosure include indicia configured as medical educational and instructional prompts that guide medical personnel through the steps of changing a central catheter insertion dressing while minimizing infection risk.

In one or more embodiments, a medical kit includes a drape with a series of pockets that are arranged side-by-side along an edge of the drape to provide maximum workspace along the drape itself. The pockets are arranged, in one embodiment, to contain medical devices in order of use during a central catheter dressing change operation. This allows the pockets to serve as a mnemonic device that alerts medical personnel to a step-by-step method for changing a central catheter dressing.

In one or more embodiments, each pocket included medical indicia affixed thereto comprising educational prompts that instruct medical personnel regarding how to use a particular device disposed within a particular pocket. For example, the medical indicia can feature animations and/or instructions that teach medical personnel how, when, and in what order to use each medical implement. In one embodiment, the pockets are additionally placed in the order of use, each containing a medical device on a one-to-one basis, and are specifically dimensioned so as to best secure the contents stowed therein. This secondarily functions in the prevention of using the medical devices in an improper order.

In one embodiment, once the medical devices are stowed within the pockets, the drape is folded, in one embodiment, with a predefined folding construct that allows the user, upon unfolding the drape, to ensure that a sterile field for the medical implements is not compromised. Illustrating by example, in one embodiment rubber gloves and liquid hand sanitizer are disposed in different folds from other medical implements, thereby ensuring that the gloves and hand sanitizer will be used before the other medical implements and in the proper order for a central catheter dressing replacement procedure. The rubber gloves and liquid hand sanitizer can be disposed in outer folds, for example, while the other implements are disposed in interior folds to ensure that the gloves and hand sanitizer are accessible before fully unwrapping the drape. In one or more embodiments, the medical kit can include other visual mnemonic devices, such as stop signs, to ensure that personnel pause during predefined portions of the procedure to complete all necessary operations of one step of the procedure prior to proceeding to a subsequent step. In one or more embodiments, the folded drape is secured in its folded form with a breakaway strip to ensure that interiorly folded portions of the drape remain sterile.

Advantageously, embodiments of the disclosure overcome problems associated with prior art central catheter dressing replacement kits. Prior art central line dressing replacement kits are not arranged in a logical fashion so as to reduce the chance of CLABSI. Moreover, they fail to include the educational prompts and other indicia advantageously offered by embodiments of the present disclosure. As such, they are non-intuitive to use and require specialized training that few medical personnel possess. These deficiencies result in variation of procedure that can result in improper dressing change procedures that increase the risk of CLABSI.

Advantages offered by the embodiments of the invention, as compared to prior art kits, include helping medical personnel more easily replace medical dressings disposed about central catheter insertion sites. Moreover, medical kits configured in accordance with one or more embodiments of the disclosure help to ensure medical personnel conformance with proper aseptic techniques. They also help in dressing replacement without compromising the integrity of the catheter that has been inserted into the patient. Other advantages and benefits will be obvious to those of ordinary skill in the art having the benefit of this disclosure.

Turning now to FIG. 1, illustrated therein is one explanatory medical kit 100 configured in accordance with one or more embodiments of the disclosure. As shown, the medical kit 100 is sealed within a wrap 101 to keep the internal components sterile. The wrap 101 can be any of a number of types of material. In one embodiment the wrap 101 comprises a thermally sealed bag. The thermally sealed bag can optionally include a preformed opening. For example, in one embodiment, the opening can include one or more tabs that a health care services provider is instructed to pull to open the bag. Sealing the contents of the medical kit 100 within the wrap not only keeps the contents within sterile, but also allows the attachment of a printed label 102 having a peelable flap 103. In one embodiment, the printed label 102 is configured as a booklet having one or more pages, with the peelable flap 103 being formed by at least one page that is peelable from at least another page.

In one or more embodiments, the printed label 102 is configured as a booklet with at least one page that is configured to be peeled away from at least another page to reveal pictorial and/or textual step-by-step instructions for using the medical kit 100. In this illustrative embodiment, the outer page of the printed label 102 includes a color photograph 104 of the contents disposed within the medical kit 100. The color photograph 104, which can also be a drawing, black and white photograph, illustration, or other rendering, is disposed in this embodiment alongside a description 105 of the medical kit 100 and an inventory 106 of at least some of the contents of the medical kit 100. In one or more embodiments the background panel 107 is a different color from the colors set forth in the color photograph 104 to emphasize the contents shown in the color photograph 104. In one embodiment, the inventory 106 of the medical kit 100 comprises a textual listing of the implements disposed within the medical kit 100.

The illustrative medical kit 100 of FIG. 1 is suitable for use in central catheter insertion site dressing changes. While this type of procedure is used in the discussion below as an illustrative application, it will be clear to those of ordinary skill in the art having the benefit of this disclosure that the invention is not so limited. Minor modification to the medical kit, such as replacement of some medical implements for others, will permit the medical kit to be readily used for a wide variety of medical procedures.

Figure 2:
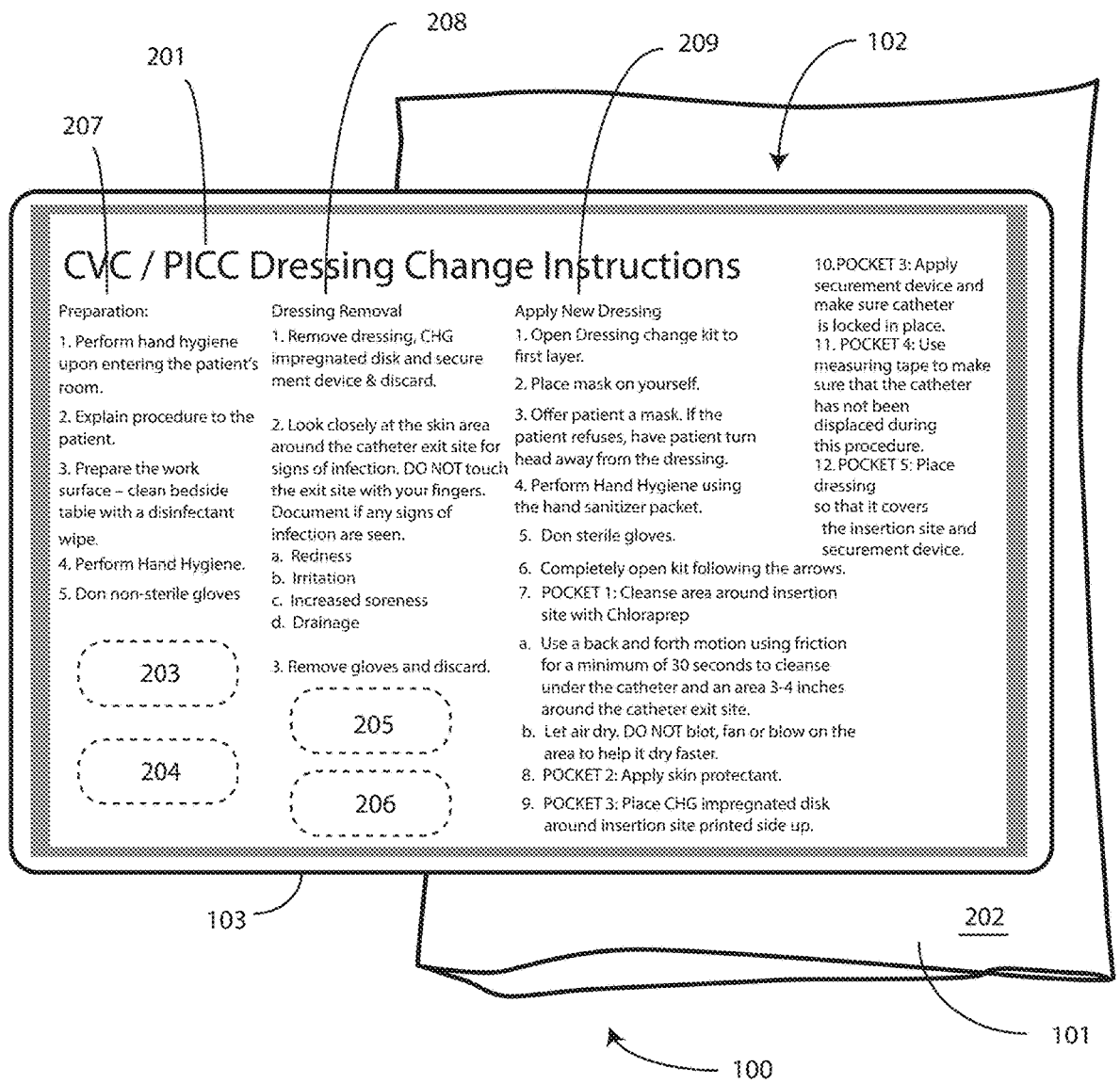
FIG. 2 illustrates one explanatory packaging label for a medical kit in accordance with one or more embodiments of the disclosure.

Turning now to FIG. 2, in one embodiment where the printed label 102 is configured as a booklet comprising at least one peelable flap 103, opening the peelable flap 103 reveals instructional material 200. The instructional material 200 can instruct medical personnel regarding how to use the medical kit 100. For example, in one embodiment the instructional material 200 includes instructions for using the medical kit 100 and the corresponding implements disposed within the medical kit 100.

Embodiments of the disclosure contemplate that placement of the printed label 102 on the outer surface 202 of the wrap 101 can be superior to placing the instructions within the wrap 101 for a variety of reasons. One illustrative reason is that patients may be less comfortable when medical personnel read the instructional material 201 corresponding to the use of the medical kit 100 in front of a patient. Even if the medical personnel is trained in what they are doing, the act of reading an instruction manual prior to performing a procedure may make the patient nervous, even questioning the medical personnel's qualifications and competence. Moreover, nervous patients can compromise the efficacy of a procedure. By making the instructional material 201 accessible prior to opening the wrap 101, medical personnel can read the same at a location away from the patient without compromising the sterility of the contents disposed within the medical kit 100.

Additionally, as noted above the contents of the medical kit 100 are sterile when sealed within the wrap 101. For procedures such as dressing replacement at central catheter insertion sites, the wrap 101 must be opened at the procedure site to avoid contamination of the medical devices disposed within the medical kit 100. Accordingly, when the instructional material 201 is disposed inside the wrap 101, a medical services provider must read the instructions in front of a patient. Adhesively affixing the printed label 102 and its instructional material 201 to the outside of the wrap 101 allows a medical services provider to refresh her memory as to the instructions without making a patient uncomfortable.

FIG. 2 provides illustrative instructional material 201 suitable for use in central catheter insertion site dressing changes. The instructional material 201 can include text only. However, in many embodiments one or more pictorial images 203,204,205,206 can be included with the text to make the instructional material 201 more easily understandable. As they say, a pictorial image 203,204,205,206 can be worth a thousand words. Accordingly, including one or more pictorial images 203,204,205,206 can reduce the amount of text needed to convey the same message.

In this illustrative embodiment, the instructional material 201 is arranged in three columnar sections 207,208,209, each including a heading and a body. In this illustrative application, the first columnar section 207 describes the steps of a preparation method to be performed before changing a central catheter insertion site dressing. For example, the body of the first columnar section 207 may include a first step instructing medical personnel to perform hand hygiene upon entering a patient's room. The body of the first columnar section 207 may include a second step instructing medical personnel to explain the procedure to a patient. The body of the first columnar section 207 may include a third step instructing medical personnel to prepare the work surface. This third step may include instructions such as cleaning a bedside table or other work surface with a disinfecting wipe. Other steps for preparing a work surface will be obvious to those of ordinary skill in the art having the benefit of this disclosure.

The body of the first columnar section 207 may include a fourth step instructing medical personnel to perform hand hygiene again. Note that the first step included a similar instruction in one embodiment above. The first hand hygiene process can be different from the second in one or more embodiments. For example, the first hand hygiene operation may be washing hands with soap and water, while the second hand hygiene operation may include the application of liquid hand sanitizer. Other hand hygiene operations will be obvious to those of ordinary skill in the art having the benefit of this disclosure. In one embodiment, the body of the first columnar section 207 may conclude by instructing medical personnel to don non-sterile gloves.

In this illustrative application, the second columnar section 208 describes the steps of removing a central catheter insertion site dressing. For example, the body of the second columnar section 208 may include a first step instructing medical personnel to remove an exterior dressing, change an impregnated disk disposed about the central catheter insertion site, and may further include instructions to properly discard both the exterior dressing and the impregnated disk.

The body of the second columnar section 208 may include a second step instructing medical personnel to examine the exposed central catheter insertion site to determine whether additional medical care is required. In this illustrative embodiment, these instructions include an instruction to look for signs of infection, including redness, irritation, increased soreness, or drainage. This second step may optionally instruct medical personnel NOT to touch the exposed central catheter insertion site with their bare fingers to help reduce CLABSI. The second step may further instruct medical personnel to document any signs of infection, including but not limited to the aforementioned redness, irritation, increased soreness, or drainage.

In this illustrative application, the third columnar section 209 describes the steps of applying a new central catheter insertion site dressing. In one embodiment, the body of the third columnar section 209 may include a first step instructing medical personnel to open the dressing kit by unfolding it to only its first layer. The body of the third columnar section 209 may then include a second step instructing medical personnel to don a surgical mask that is included within a first exterior fold of the dressing kit. The body of the third columnar section 209 may then include a third step instructing medical personnel to offer the patient a mask. The third step may further instruct medical personnel to instruct the patient, if a mask is refused, to turn away from the central catheter insertion site.

The body of the third columnar section 209 may include a fourth step instructing medical personnel to perform hand hygiene using liquid hand sanitizer disposed within the first exterior fold of the dressing kit. As will be shown in more detail below with reference to FIGS. 8-10, in one or more embodiments a surgical mask, liquid hand sanitizer, and sterile disposable gloves are strategically placed within a first exterior fold of the dressing kit while other implements used in the central catheter insertion site dressing change are disposed within second, third, or fourth interior folds of the dressing kit. Accordingly, in one or more embodiments the fourth step of the body of the third columnar section may correspond directly to a physical location within the dressing kit where specific medical implements are disposed.

In one embodiment, the body of the third columnar section 209 may then include a fifth step instructing medical personnel to don sterile gloves disposed within the first exterior fold of the dressing kit. In one embodiment, the body of the third columnar section 209 may then include a sixth step instructing medical personnel to completely open kit using a breakaway strip by initiating a tear following the arrows.

In one embodiment, the body of the third columnar section 209 may then include a seventh step instructing medical personnel to cleanse the area around a central catheter insertion site using an implement disposed within a first pocket of the dressing kit. This seventh step may include substeps such as "Use a back and forth motion using friction to cleans an area under the catheter and an area 3-4 centimeters for a minimum of 30 seconds, and "Let air dry. DO NOT blot, fan or blow on the around the catheter exit site to help it dry faster." Other central catheter insertion site cleansing steps will be obvious to those of ordinary skill in the art having the benefit of this disclosure.

In one embodiment, the body of the third columnar section 209 may then include a seventh step instructing medical personnel to use an implement disposed within a second pocket of the dressing kit to apply a skin protectant. In one embodiment, the body of the third columnar section 209 may then include a eighth step instructing medical personnel to use an implement disposed within a third pocket of the dressing kit to apply an impregnated disk around insertion site printed side up. The eighth step may also include an instruction to apply a securement device to make sure the catheter is locked in place.

In one embodiment, the body of the third columnar section 209 may then include a ninth step instructing medical personnel to use an implement disposed within a fourth pocket of the dressing kit to measure a distance between the central catheter insertion site and a reference point to ensure that the central catheter has not been disturbed or its placement altered during the dressing replacement procedure. In one embodiment, the body of the third columnar section 209 may then include a tenth step instructing medical personnel to use an implement disposed within a fifth pocket of the dressing kit to place a dressing so that it covers the insertion site and securement device. It should be noted that these instructions are illustrative only, as others will be readily obvious to those of ordinary skill in the art having the benefit of this disclosure.

It should be noted that the instructional material 201 disposed within the booklet defined by the printed label 102 is defined as medical personnel instructions, as it is directed to medical personnel who are performing the dressing change operation. However, embodiments of the disclosure contemplate that it can be advantageous to include other types of instructions as well. For example, the inclusion of instructional material specifically targeted at a patient, rather than medical personnel, can further reduce the chance of CLABSI.

Figure 3:
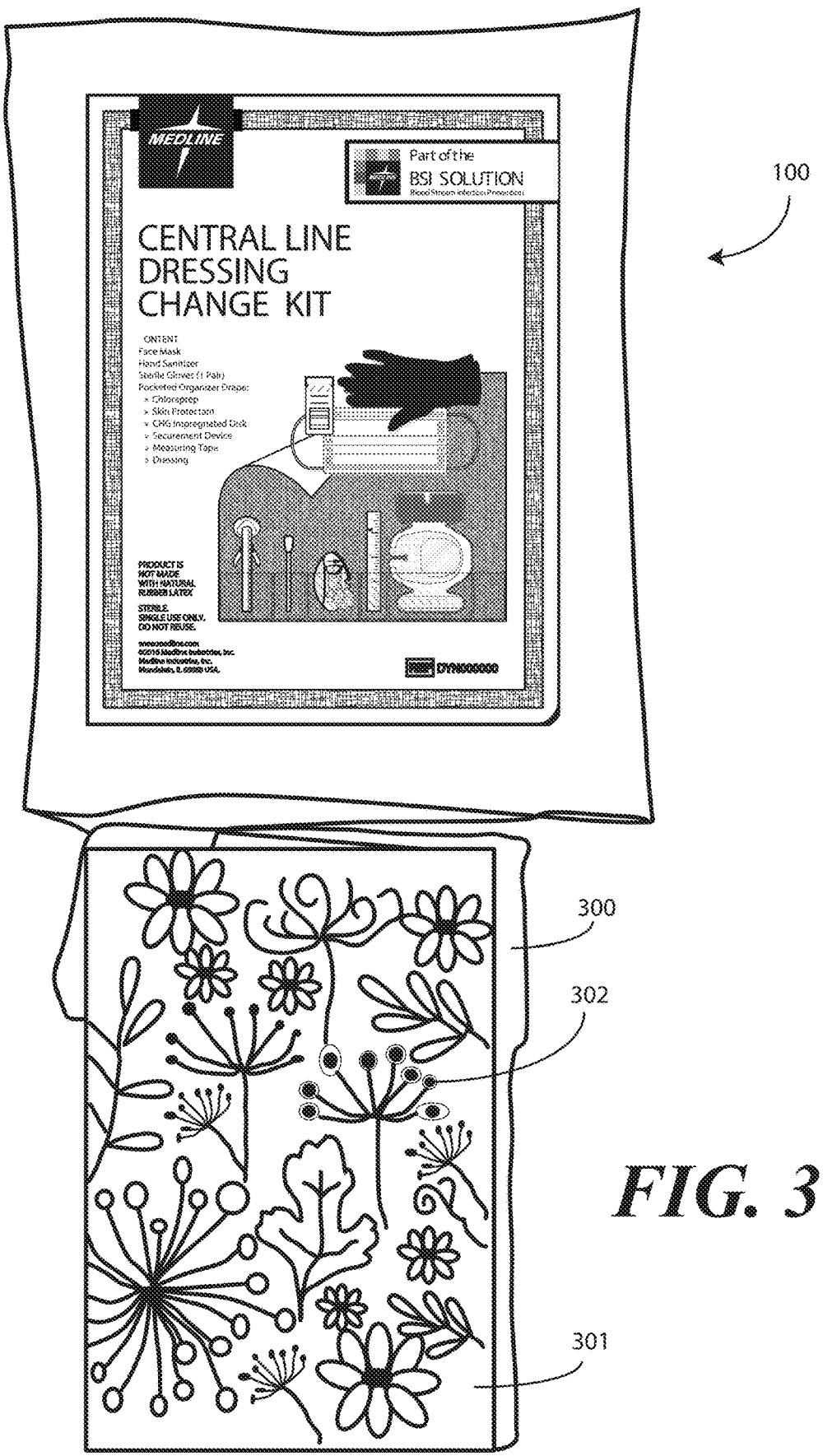
FIG. 3 illustrates explanatory contents of a medical kit in accordance with one or more embodiments of the disclosure.

Turning now to FIG. 3, the wrap 101 has been opened and the dressing kit 300 and patient instructional material 301 have been removed from the wrap 101. As will be shown in more detail below with reference to FIG. 4, the patient instructional material 301 can include helpful suggestions or instructions for the patient into whom the central catheter is inserted. As shown in FIG. 3, in this illustrative embodiment the patient instructional material 301 is separate and distinct from the instructional material (201) directed toward medical personnel. Accordingly, the patient instructional material 301 can be given to the patient to keep.

In this illustrative embodiment, the patient instructional material 301 is configured as a booklet. In one embodiment, the patient instructional material 301 is configured with a greeting card appearance. While some embodiments can provide patient instructional material 301 that is very straightforward, informational, and clinical in nature, in the embodiment of FIG. 3 the patient instructional material 301 is configured as a greeting card.

Embodiments of the disclosure contemplate that when patient instructional material is configured as plain text on a plain white background it is less likely to be delivered to the patient. Medical personnel may mistake it for the instructional material (201) directed to the procedure rather than the patient. However, by configuring the patient instructional material 301 as a greeting card, such as with a pleasant picture 302 of flowers or similar objects on the front and stylized text providing the information therein, it is more likely to be given to the patient. Thus, configuring the patient instructional material 301 as a greeting card helps to reduce CLABSI.

In addition to a pleasant picture 302, the exterior of the patient instructional material can include an inspirational phrase and/or one or more aesthetically pleasing images. One example of an aesthetically image is a vase of flowers. Others will be obvious to those of ordinary skill in the art having the benefit of this disclosure. For example, other aesthetically pleasing images could include puppies, sunsets, mountain streams, and so forth. In one or more embodiments, the patient instructional materials may include a textual identifier informing the patient of the purpose of the patient instructional materials.

Figure 4:
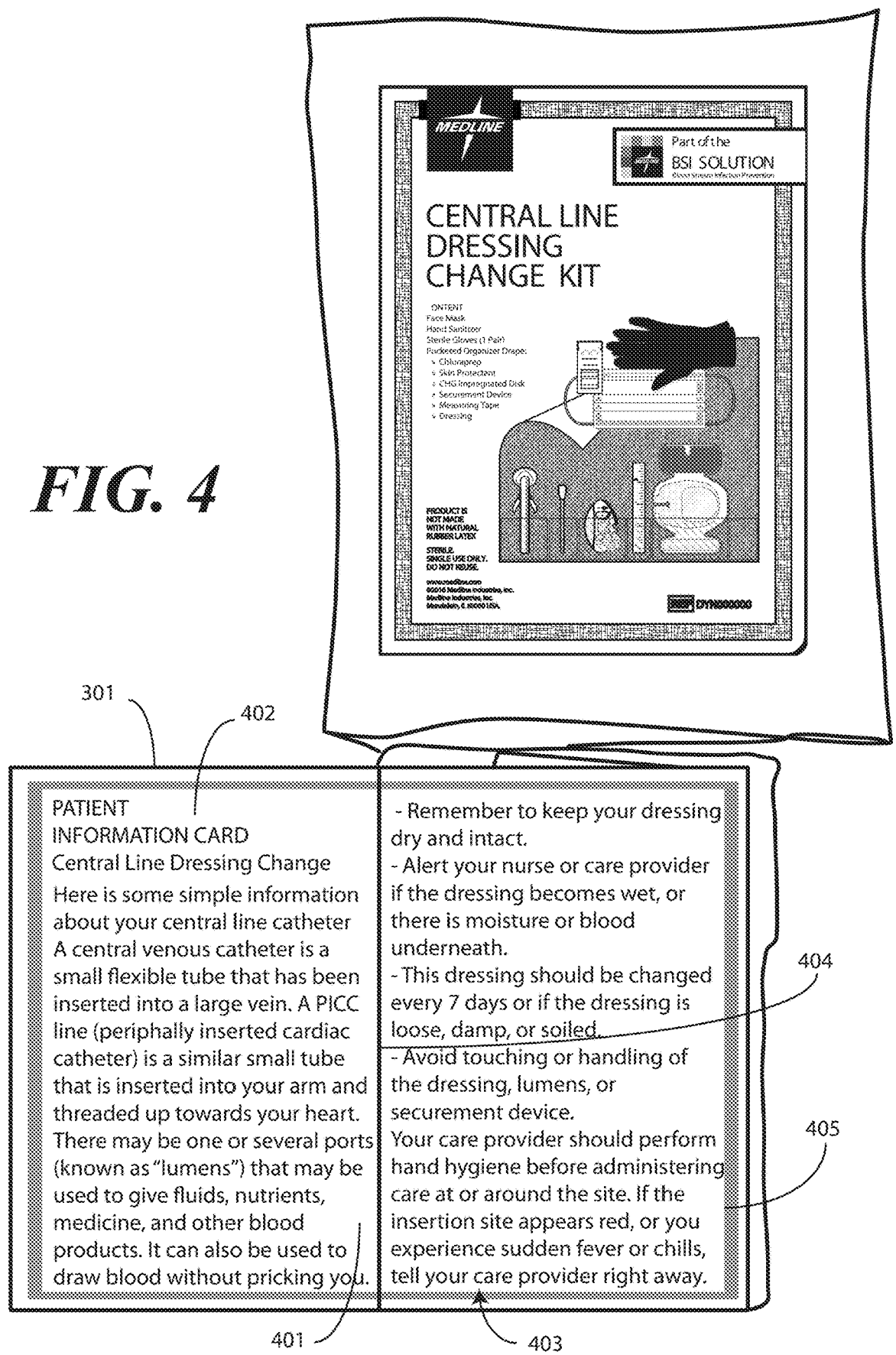
FIG. 4 illustrates one explanatory patient care card of a medical kit in accordance with one or more embodiments of the disclosure.

The patient instructional materials 301 can include helpful suggestions or instructions for the patient. The patient instructional material 301 can be configured with a greeting card appearance to make the information more pleasantly received by a patient. Examples of suggestions or instructions that may be included in the patient portion include information on what a central catheter is, what the patient should understand about the central catheter, how to reduce the chance of getting an infection, information about infections commonly associated with central catheters, and symptoms of infections commonly associated with central catheters. Turning now to FIG. 4, one example of a set of helpful suggestions suitable for use with one or more embodiments of the disclosure.

As shown in FIG. 4, when the greeting card defined by the patient instructional material 301 is opened, the interior can provide helpful suggestions 401 suitable for describing patient actions that help reduce the chances of CLABSI in conjunction with central catheter insertion site dressing changes. The helpful suggestions 401 can include text only. However, as was the case with the instructional material (201) for medical personnel, in many embodiments one or more pictorial images can be included with the textual information to make the helpful suggestions 401 more easily understandable.

In this illustrative embodiment, the helpful suggestions 401 are arranged in two columnar sections 302,302, arranged on opposite sides of a fold 304 within a colorful banner 305. In this illustrative application, the two columnar sections 302,303 provide suggestions or instructions regarding what a central catheter is, what the patient should understand about the central catheter, how to reduce the chance of getting an infection, information about infections commonly associated with central catheters, and symptoms of infections commonly associated with central catheters.

In this illustrative embodiment, the two columnar sections 302,303 include only text. IN one embodiment, the first columnar section 302 includes the following illustrative text: "Here is some simple information about your central line catheter. A central venous catheter is a small flexible tube that has been inserted into a large vein. A PICC line (peripherally inserted cardiac catheter) is a similar small tube that is inserted into your arm and threaded up towards your heart. There may be one or several ports (known as "lumens") that may be used to give fluids, nutrients, medicine, and other blood products. It can also be used to draw blood without pricking you again." In one illustrative embodiment, the second columnar section 303 includes the following illustrative text: "Remember to keep your dressing dry and intact. Alert your nurse or care provider if the dressing becomes wet, or there is moisture or blood underneath. This dressing should be changed every 7 days or if the dressing is loose, damp, or soiled. Avoid touching or handling of the dressing, lumens, or securement device. Your care provider should perform hand hygiene before administering care at or around the site. If the insertion site appears red, or you experience sudden fever or chills, tell your care provider right away."

The above information on the patient instructional materials 301 and/or the instructional materials 201 can be printed in multiple languages, such as in Spanish or in English. Further, alternatives and variations of the information can be substituted for the example set forth above. It should be noted that these instructions are illustrative only, as others will be readily obvious to those of ordinary skill in the art having the benefit of this disclosure.

Figure 5:
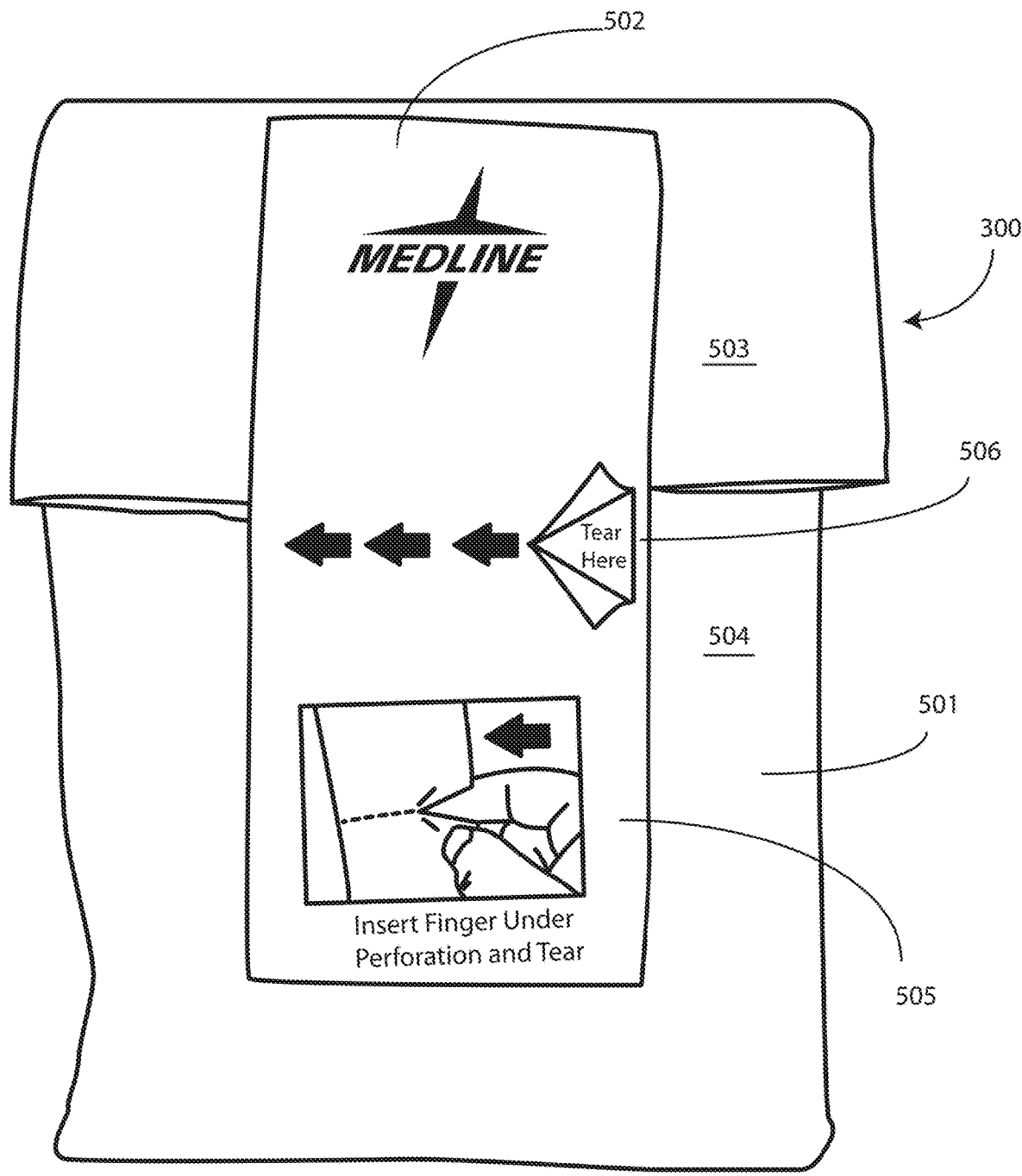
FIG. 5 illustrates explanatory contents of a medical kit in accordance with one or more embodiments of the disclosure.

Turning now to FIG. 5, once the patient instructional material (301) has been given to the patient and the wrap (101) discarded, the dressing kit 300 remains. As shown in FIG. 5, in one embodiment the dressing kit 300 comprises a folded drape 501 that is sealed with a breakaway strip 502. In this illustrative embodiment, the breakaway strip 502 is adhesively affixed to the folded drape 501 to keep a first upper exterior portion 503 folded atop a second upper exterior portion 504. As will be described in more detail below, in one or more embodiments some medical implements are disposed within more exterior folds while other medical implements are disposed within more interior folds. The breakaway strip 502 ensures that those items stowed within the more exterior folds are securely retained within the folded drape 501 until needed.

In one embodiment, the folded drape 501 is opaque. The folded drape 501 can be color-coded to indicate that it is designed for a particular procedure as well. For example, a particular color such as blue may indicate that the dressing kit 300 is to be used for a central catheter inserted into a patient's chest, while a green drape may indicate that the dressing kit it to be used with a peripherally inserted central catheter. Other color codings will be obvious to those of ordinary skill in the art having the benefit of this disclosure.

In one embodiment, the folded drape 501 can be manufactured from any type of flat cloth, including those manufactured from any of woven materials, nonwoven materials, or combinations thereof. Examples of nonwoven materials include spunbound materials, meltblown materials, or combinations thereof. Such materials are well known in the art. Additionally, the material weight of the folded drape 501 can vary as well. For example, in one illustrative embodiment the folded drape is manufactured from a non-woven material having a weight of between ten and one hundred grams per square meter.

In another embodiment, the folded drape 501 can be manufactured from 60-gram, plus or minus two grams, spunbond-meltblown-spunbond material. Other materials can be used for the folded drape 501, including, for example, various woven, non-woven, hydroentangled materials, and/or combinations thereof, absorbent Airlaid, spunlace, blends of polyester, polypropylene, polyethylene, urethane, and/or combinations thereof, using various methods, including a spunbond meltblown spundbond (SMS) method, a spunbond meltblown metlblown spundbond method (SMMS), and a spunbond metlblown metlblown meltblownspundbond method (SMMMS). Other materials, such as plastic, cotton, linen, paper, or combinations thereof, can be substituted.

These materials and methods are illustrative only, as others will be readily apparent to those of ordinary skill in the art having the benefit of this disclosure. For example, one or more antimicrobial layers can be added to the folded drape 501 to further enhance antimicrobial protection. Additionally, the material can optionally include and water resistant lining that prevents the passage of fluids through the material of the folded drape 501. In one or more embodiments, the folded drape 501, when unfolded, has a length of between sixteen and twenty centimeters, such as about seventeen and a half centimeters plus or minus an inch. In one embodiment, the patient drape has a width of between nineteen and twenty three centimeters, such as about twenty-one and a half centimeters, plus or minus one inch.

In one or more embodiments, the breakaway strip 502 includes both instructional indicia 505 for opening the folded drape 501 and sever targets 506. In this embodiment, the instructional indicia 505 comprises a pictorial representation of how a finger can be used to separate the breakaway strip 502 by tearing along the sever targets 506. In this illustrative embodiment, the sever targets 506 comprise three solid arrows that follow a severing wedge circumscribing the words "tear here." While this is one embodiment of sever targets in accordance with embodiments of the disclosure, others will be obvious to those of ordinary skill in the art having the benefit of this disclosure. A user opens the initial fold of the folded drape 501 by placing their finger at the severing wedge and tearing the breakaway strip along a line defined by the three solid arrows.

Figure 6:
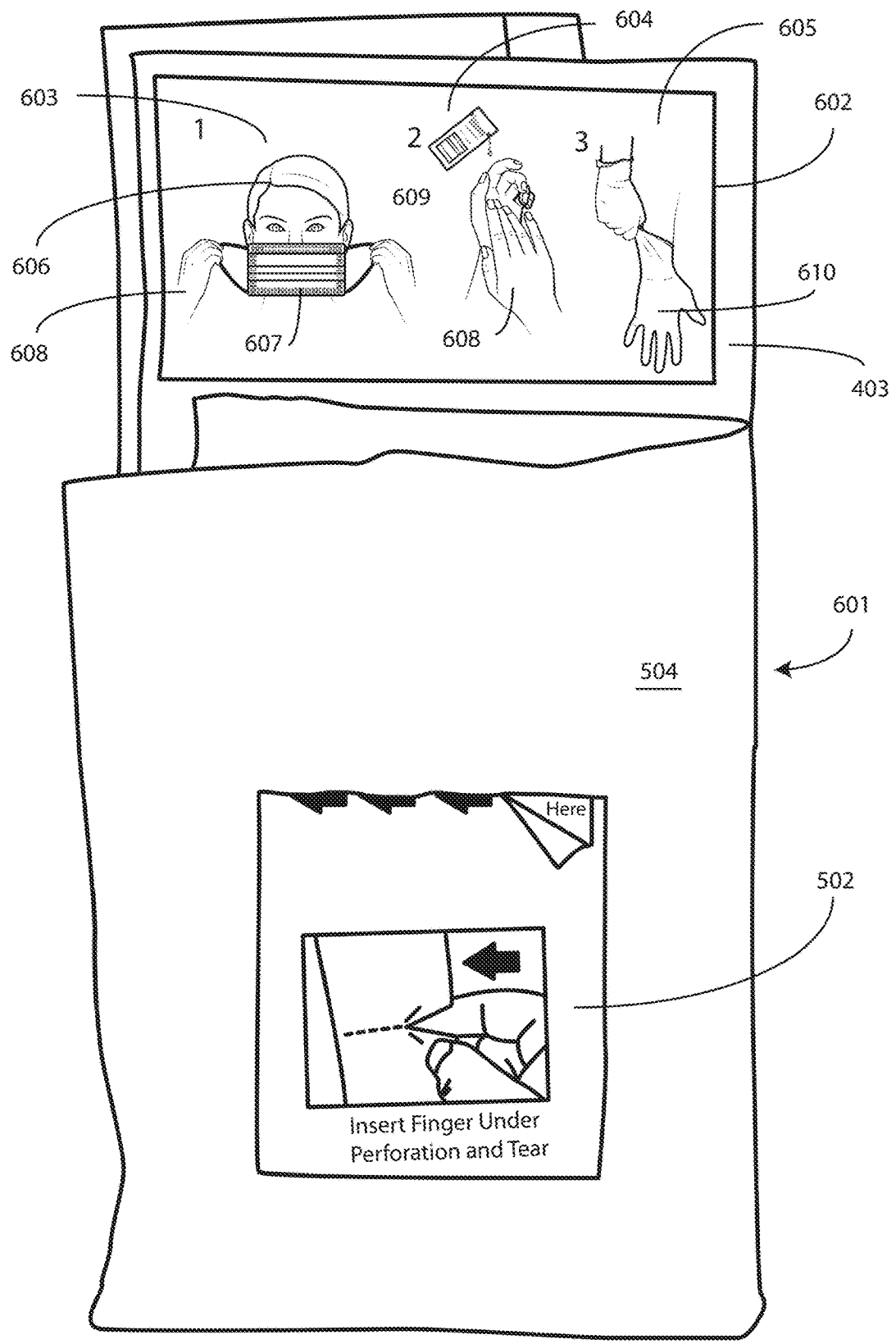
FIG. 6 illustrates explanatory contents of a medical kit in accordance with one or more embodiments of the disclosure.
Figure 13:
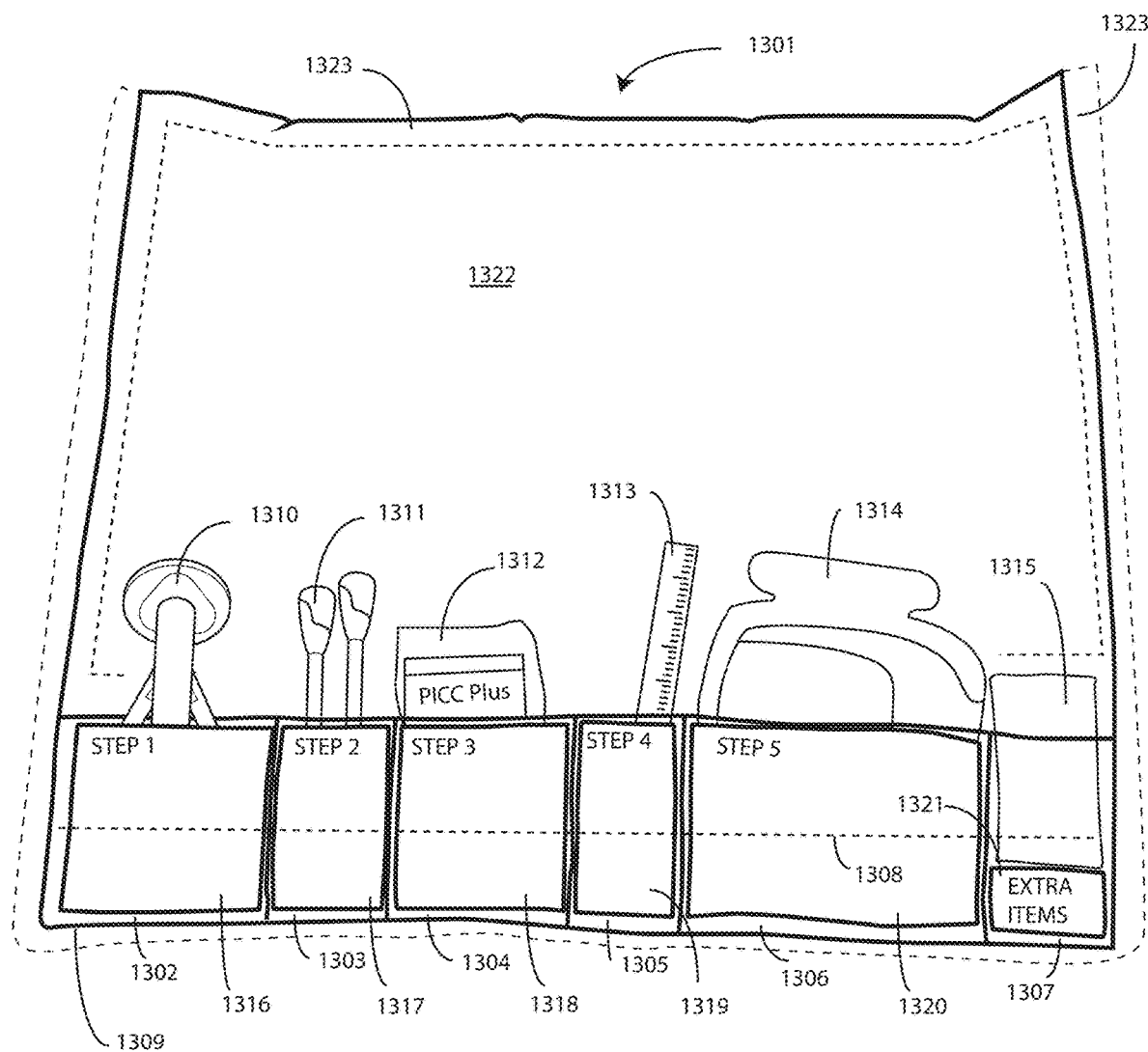
FIG. 13 illustrates explanatory contents of a medical kit in accordance with one or more embodiments of the disclosure.

Turning now to FIG. 6, once the breakaway strip 502 is severed, the first upper exterior portion 503 of the folded drape can be unfolded from atop a second upper exterior portion 504 to transform the folded drape (501) into a first partially folded drape 601. As subsequent figures are described, the folded drape (501) transforms to a first partially folded drape 601, a second partially folded drape, a third partially folded drape, and so forth, until finally transforming into a fully unfolded drape as shown in FIG. 13, or alternatively in FIGS. 19-20. Accordingly, the unfolding steps described in these transformations represent process descriptions and/or flow charts of one or more methods for transforming the folded drape (501) into an unfolded drape for use. Additionally, these steps or processes can be performed in reverse order to construct the folded drape (501) from an initially folded drape. Thus, methods and descriptions for these processes have been described herein. Further, it is expected that one of ordinary skill, notwithstanding possibly significant effort and many design choices motivated by, for example, available time, current technology, and economic considerations, when guided by the concepts and principles disclosed herein will be readily capable of performing such methods with minimal experimentation.

In one or more embodiments, the initial unfolding step from the configuration of the folded drape (501) reveals first medical indicia 602. As noted above, in one or more embodiments elements of the medical kit (100) can include medical indicia 602 affixed thereto comprising one or more educational prompts 603,604,605 that instruct medical personnel regarding how to use a particular element or device of the medical kit (100). Such is the case here. In this illustrative embodiment, the educational prompts 603,604, 605 features animations and/or instructions that teach medical personnel how, when, and in what order to use a particular medical implement.

In the embodiment of FIG. 6, the first educational prompt 603 instructs medical personnel to don a surgical mask. The first educational prompt 603 of this embodiment illustrates a medical services provider 606 holding a surgical mask 607 with their hands 608 right before placing the surgical mask 607 over their mouth and nose. Advantageously, the use of an animated instruction as the first educational prompt 603 ensures that the instructions embodied therein transcend language barriers. Regardless of the language spoken, medical personnel will readily understand that the animation of a medical services provider 606 holding a surgical mask 607 with their hands 608 right before placing the surgical mask 607 over their mouth and nose is an instruction to don a surgical mask.

Similarly, the second educational prompt 604 provides an animation of the application of liquid hand sanitizer 609 to the hands 608 of the medical service provider 606. The third educational prompt 605 illustrates the medical service provider 606 donning gloves 610 over their hands 608.

The location of the medical indicia 602 can be important in many applications. In the illustrative embodiment of FIG. 6, due to the way the folded drape (501) was folded with the a first upper exterior portion 403 folded atop a second upper exterior portion 404, the only logical unfolding operation that can be performed is to unfold the first upper exterior portion 403 of the folded drape (501) from atop a second upper exterior portion 404 to transform the folded drape (501) into a first partially folded drape 601. In this embodiment, the medical indicia is disposed under the first upper exterior portion 403 so that it is revealed and becomes immediately visible when the first upper exterior portion 403 of the folded drape (501) is unfolded from atop a second upper exterior portion 404. This location does three things: First, it alerts medical personnel to the fact that medical devices are likely to be revealed in the next unfolding step. Second, it prevents the first partially folded drape 601 from being opened "upside down" by the user in that the medical indicia can only be read when the first partially folded drape 601 is in one orientation. Third, it instructs medical personnel regarding both what medical implements will be revealed in subsequent unfolding steps and in what order they should be used to preserve the sterile field required for central catheter dressing replacement. This latter function also works to prevent the use of medical devices in an improper order, which may contribute to the sterile field being compromised.

Figure 7:
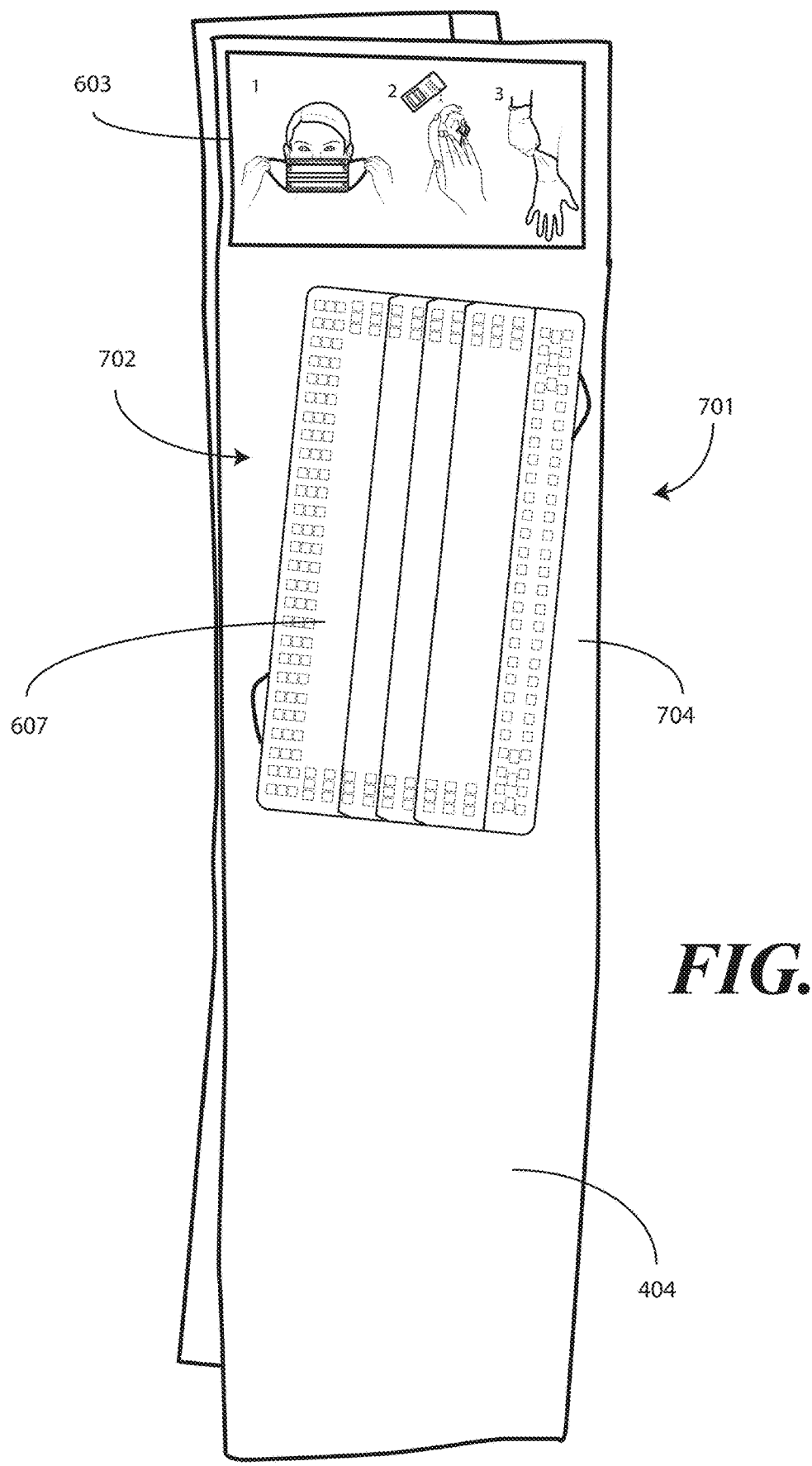
FIG. 7 illustrates explanatory contents of a medical kit in accordance with one or more embodiments of the disclosure.

Turning now to FIG. 7, the second upper exterior portion 404 is unfolded from atop a central exterior portion 704 to transform the first partially folded drape (601) into a second partially folded drape 701. In this illustrative embodiment, this second unfolding step from the configuration of the first partially folded drape (601) reveals a medical device cluster

702. Disposed atop the medical device cluster 702 is a surgical mask 607. This is consistent with instruction provided by the first educational prompt 603, which indicates that the first step medical personnel should take is donning the surgical mask 607. Accordingly, by unfolding the second upper exterior portion 404 from atop a central exterior portion 704 to transform the first partially folded drape (601) into a second partially folded drape 701, medical personnel has instant access to the surgical mask 607 so that it can be donned.

Figure 8:
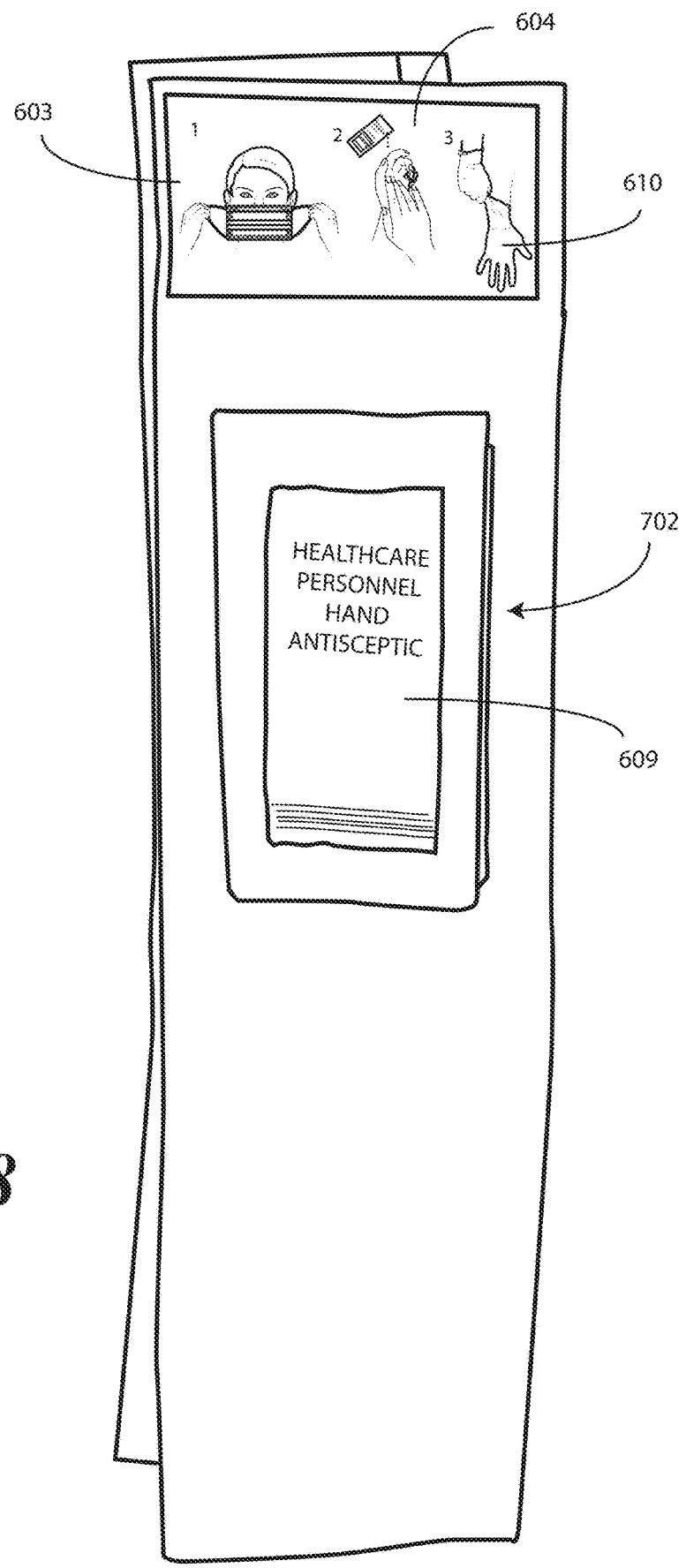
FIG. 8 illustrates explanatory contents of a medical kit in accordance with one or more embodiments of the disclosure.

Turning now to FIG. 8, the surgical mask (607) has been removed from the medical device cluster 702 and donned in accordance with the instruction provided by the first educational prompt 603. In one embodiment, this reveals liquid hand sanitizer 609, which was disposed beneath the surgical mask (607). Accordingly, removal of the surgical mask reveals the liquid hand sanitizer, which is consistent with the instruction provided by the second educational prompt 604 to apply hand sanitizer after donning the surgical mask (607) and before donning gloves 610.

Figure 9:
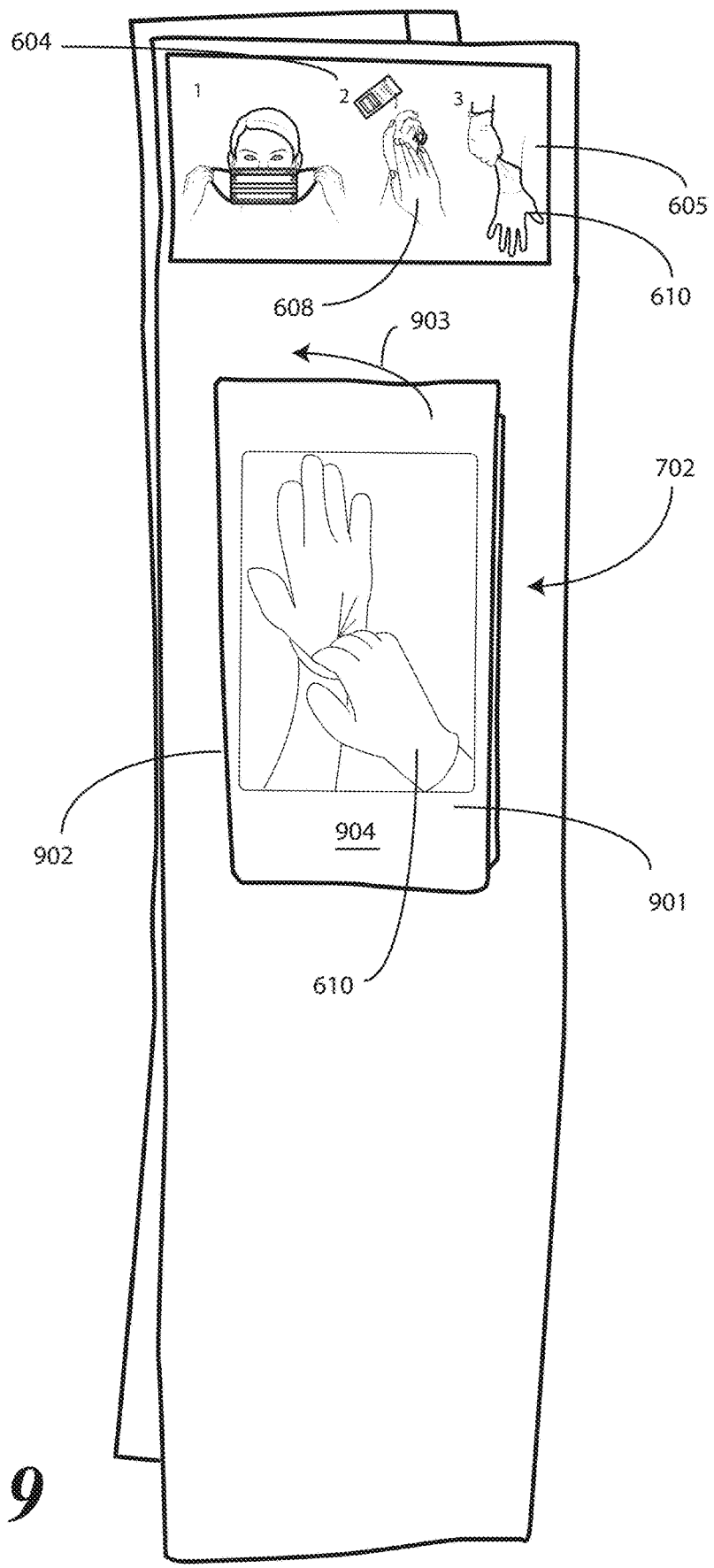
FIG. 9 illustrates explanatory contents of a medical kit in accordance with one or more embodiments of the disclosure.

Turning now to FIG. 9, the liquid hand sanitizer (609) has been removed from the medical device cluster 702 and applied to the hands 608 in accordance with the instruction provided by the second educational prompt 604. In the illustrative embodiment of FIG. 9, this reveals a package 901 of sterile rubber gloves 610, which was disposed beneath the package of liquid hand sanitizer (609). This step of revealing the package 901 of sterile rubber gloves 610 is consistent with the instruction provided by the third educational prompt 605 to don rubber gloves 610 after applying the liquid hand sanitizer (609) to the hands (608).

In this illustrative embodiment, the package 901 in which the rubber gloves 610 are disposed comprises a folded package rather than a sealed package. Embodiments of the disclosure contemplate that if the package 901 is sealed, a user may attempt to pick it up and tear it, potentially away from the sterile field. To prevent this, in one embodiment the package 901 comprises a folded package with a central book fold 902 on one side of the package 901. Medical personnel may lift 903 the top portion 904 of the package 901 to unfold the central book fold 902.

Figure 10:
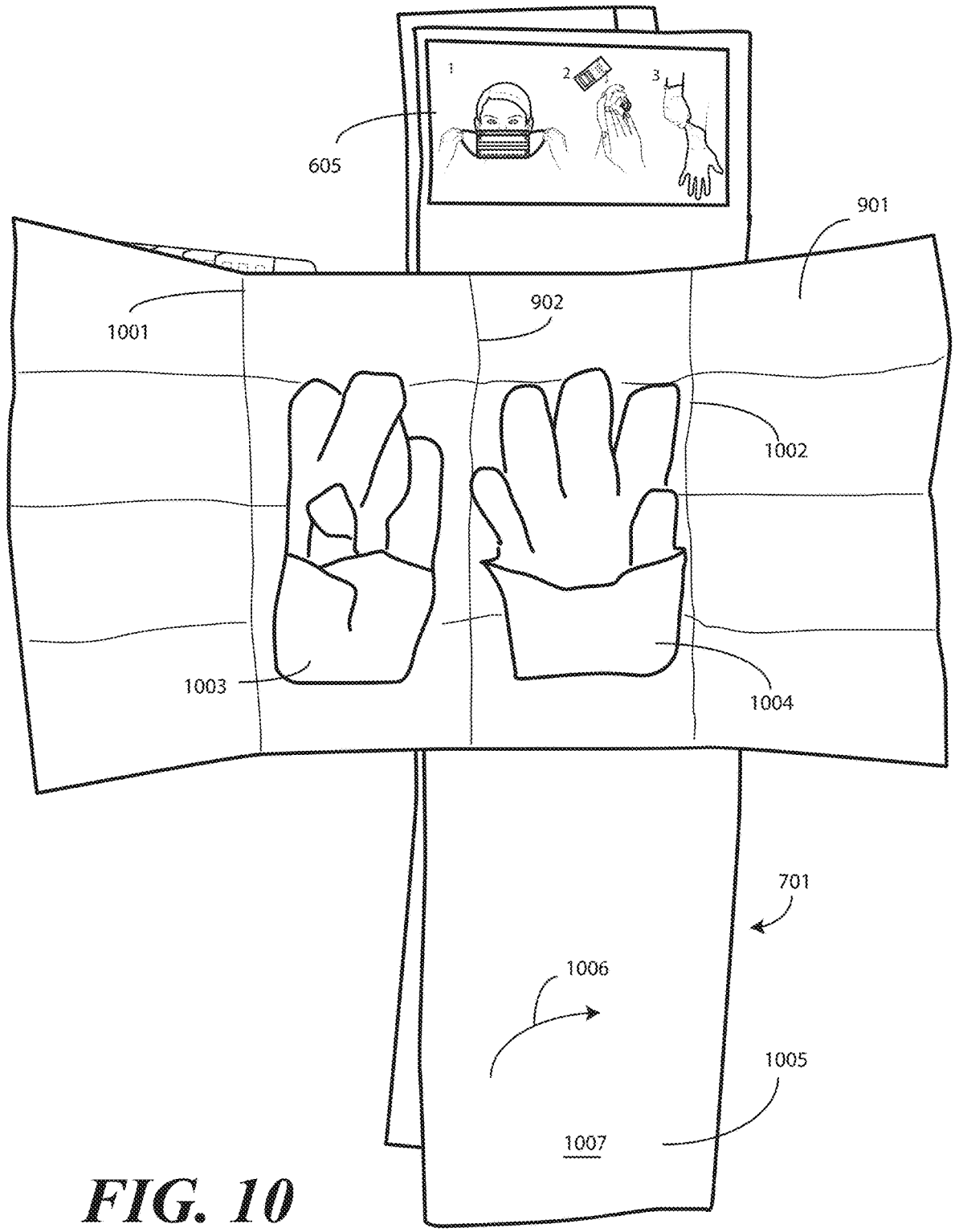
FIG. 10 illustrates explanatory contents of a medical kit in accordance with one or more embodiments of the disclosure.

Turning now to FIG. 10, illustrated therein is the package 901 once fully opened. As shown in FIG. 10, the central book fold 902 is disposed between a first outer book fold 1001 and a second outer book fold 1002, respectively. In this illustration, each of the first outer book fold 1001 and the second outer book fold 1002 has been opened to reveal two rubber gloves 1003,1004. Each of the rubber gloves 1003, 1004 is partially turned inside out to make donning the same simpler. Accordingly, by unfolding the central book fold 902, the first outer book fold 1001, and the second outer book fold 1002, the rubber gloves 1003,1004 are revealed so that they can be donned in accordance with the instruction provided by the third educational prompt 605.

Just as the package 901 for the rubber gloves 1003,1004 comprised a central book fold 902, so too does the second partially folded drape 701. In this illustrative embodiment, the central book fold 1005 of the second partially folded drape 701 is disposed along the right side of the second partially folded drape 701. Medical personnel may lift 1006 the top portion 1007 of the second partially folded drape 701 to unfold the central book fold 1005. The result, which is a third partially folded drape 1101, is shown in FIG. 11.

Figure 11:
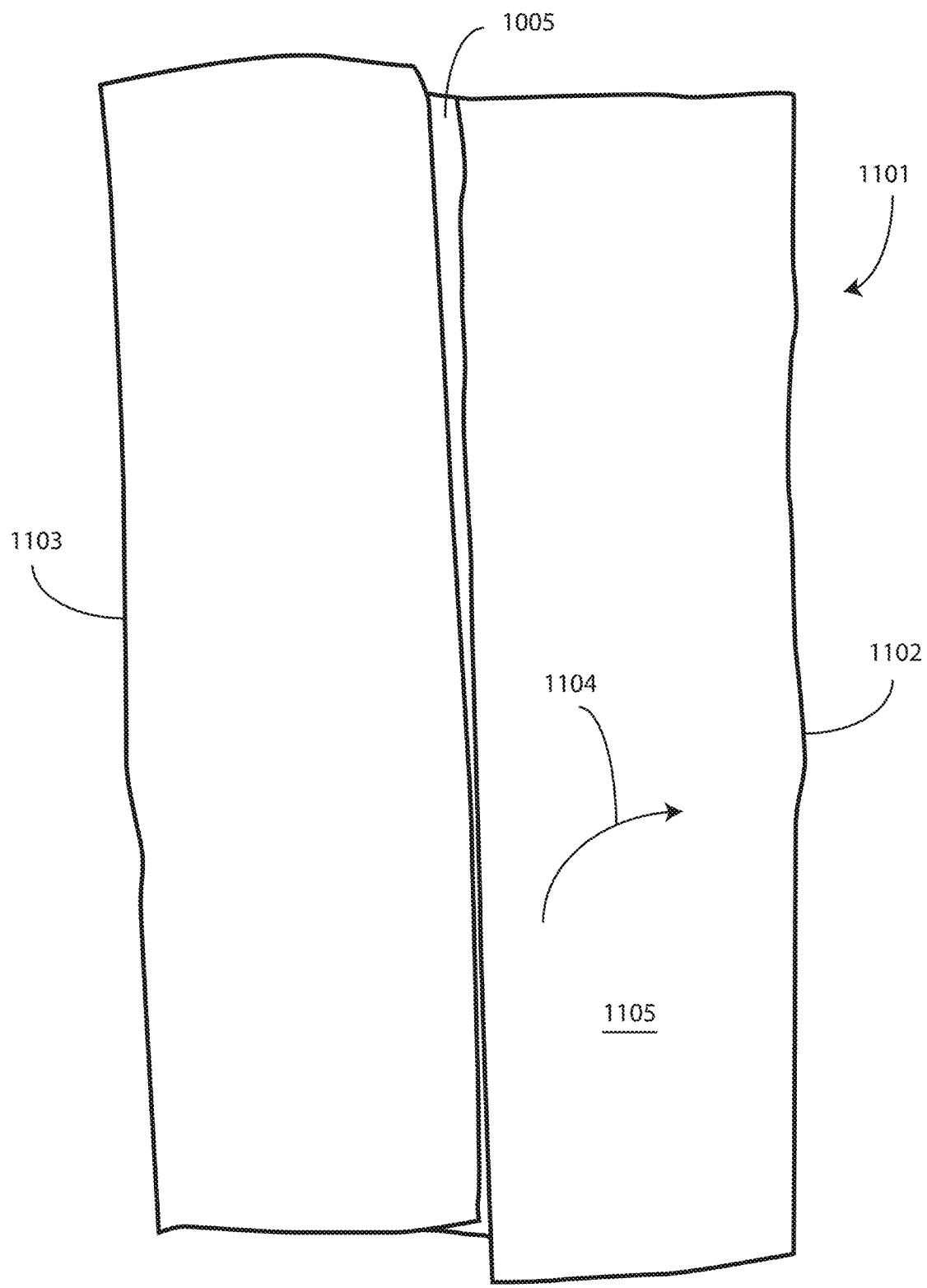
FIG. 11 illustrates explanatory contents of a medical kit in accordance with one or more embodiments of the disclosure.
Figure 12:
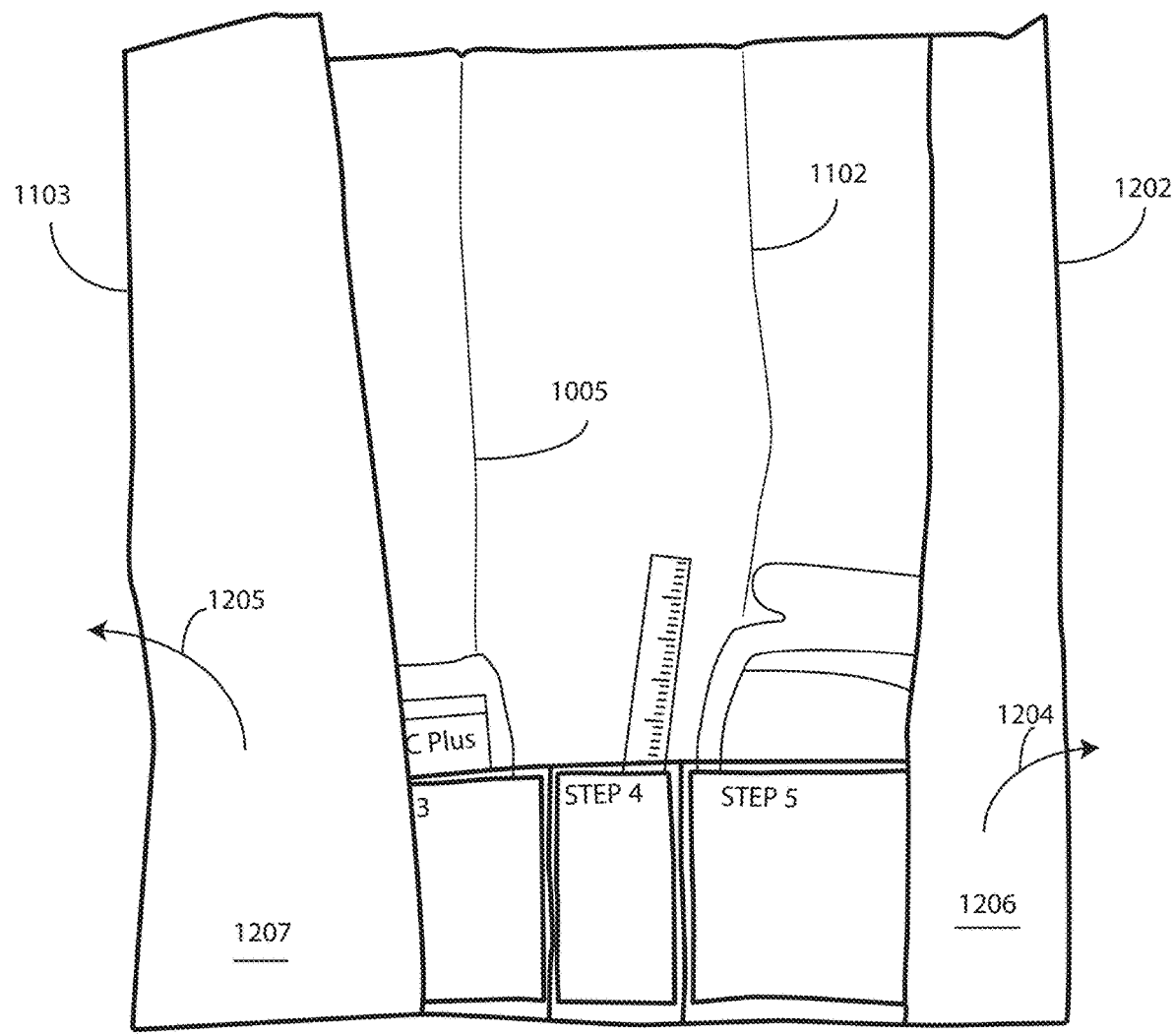
FIG. 12 illustrates explanatory contents of a medical kit in accordance with one or more embodiments of the disclosure.

Turning now to FIG. 11, in one or more embodiments the central book fold 1005 of the second partially folded drape (701) of is disposed between a first outer book fold 1102 and a second outer book fold 1103 of the third partially folded drape 1101, respectively. As with the central book fold 1005, medical personnel may lift 1104 the top portion 1105 of the third partially folded drape 1101 to unfold the first outer book fold 1102. The result, which is a fourth partially folded drape 1201, is shown in FIG. 12. It should be noted that, in one or more embodiments, additional use instructions or medical supplies can be disposed within these folds as was the case with the package (901) of rubber gloves (1003, 1004) or the medical indicia (602) described above.

Turning now to FIG. 12, it can be seen that the first outer book fold 1102 is disposed between the second outer book fold 1103 and a third outer book fold 1202. Additionally, the first outer book fold 1102 is disposed between the third outer book fold 1202 and the central book fold 1005. This type of folding ensures that a first indicia panel 1203 is defined between the first outer book fold 1102 and the third outer book fold 1202 onto the reverse side of which the medical indicia (602) may be attached. Medical personnel may lift 1204,1205 the top remaining portions 1206,1207 of the fourth partially folded drape 1201 to unfold the third outer book fold 1202 and the second outer book fold 1103, respectively. The result, which is an unfolded drape 1301, is shown in FIG. 13. An alternate unfolded drape will be discussed below with reference to FIGS. 19-20.

As shown in FIG. 13, the unfolded drape 1301 includes the drape 1323 itself. In one embodiment, a series of pockets 1302,1303, 1304,1305,1306,1307 disposed along the drape 1323 in a linear, side-by-side arrangement 1308 along a bottom edge 1309 of the unfolded drape 1301. In some embodiments, additional material 1324 could extend beyond the sides of the series of pockets 1302,1303,1304,1305,1306 to ensure that the contents in the series of pockets 1302, 1303,1304,1305,1306 remain sterile when the unfolded drape 1301 is folded. Disposing each of the pockets 1302, 1303,1304,1305,1306,1307 along the base of the unfolded drape 1301 advantageously leaves a maximized, sterile work surface 1322 upon which medical personnel may work when changing a central catheter insertion site dressing.

In this illustrative embodiment, the series of pockets 1302,1303,1304,1305,1306,1307 comprises six pockets. In other applications, the number of pockets may be greater than six pockets, or fewer, depending upon application. For example, if the medical implement 1313, i.e., the ruler, is not required, and the medical indicia 1319 disposed on the fourth pocket 1305 instead includes instructions on how to use the gradients on the catheter to measure distances, this pocket may be modified or eliminated. Other reconfigurations to the number or purpose of the series of pockets 1302,1303,1304,1305,1306,1307 will be obvious to those of ordinary skill in the art having the benefit of this disclosure.

Each pocket holds a medical implement 1310, 1311,1312, 1313,1314,1315 on a one-to-one basis, with those medical implements 1310,1311, 1312,1313,1314,1315 arranged in accordance with a predefined order of use in a central catheter dressing change procedure. In other embodiments, each pocket may hold multiple medical implements. Accordingly, medical personnel can start from the left, drawing a first medical implement 1310 from the first pocket 1302, and complete a first step of the central catheter dressing change procedure. Medical personnel can then move to the second pocket 1303, draw a second medical implement 1311, and so forth, to successfully complete the central catheter dressing change procedure.

In this illustrative embodiment, the series of pockets 1302,1303,1304,1305,1306,1307 are formed and defined by thermally bonding a clear plastic film to the unfolded drape 1301. In other embodiments, the series of pockets 1302,

1303,1304,1305,1306,1307 are glued to the unfolded drape 1301. In still other embodiments, the series of pockets 1302,1303,1304,1305,1306,1307 are stitched to the unfolded drape 1301. Still other techniques for bonding the series of pockets 1302,1303,1304,1305,1306,1307 to the unfolded drape 1301 will be obvious to those of ordinary skill in the art having the benefit of this disclosure.

It should be noted that the sizes and widths of the series of pockets 1302,1303,1304,1305, 1306,1307 can be varied as well. For example, pocket 1306, which includes medical implement 1314, may be widened so that this medical implement 1314 does not fold when the first outer book fold (1102) is applied. Other modifications to the width and extent of the series of pockets 1302,1303,1304,1305,1306, 1307 will be obvious to those of ordinary skill in the art having the benefit of this disclosure.

In one embodiment, each pocket 1302,1303,1304,1305, 1306,1307 has medical indicia 1316,1317,1318,1319,1320, 1321 attached thereto. The medical indicia 1316,1317,1318, 1319, 1320,1321 each comprise one or more educational prompts (described below with reference to FIGS. 14-18) that instruct medical personnel regarding how to use a particular medical implement disposed in a pocket to which the medical indicia is attached. Illustrating by example, medical indicia 1316, which is attached to pocket 1302, comprises an educational prompt that instructs medical personnel regarding how to use medical implement 1310, which is stowed in pocket 1302. Similarly, medical indicia 1317, which is attached to pocket 1303, comprises one or more educational prompts instructing medical personnel how to use medical implement 1311, and so forth. As each medical implement 1310, 1311,1312,1313,1314,1315 is stowed in each pocket 1302,1303,1304,1305,1306,1307 on a one-to-one basis in this embodiment, with those medical implements 1310,1311,1312,1313,1314, 1315 arranged in accordance with a predefined order of use in a central catheter dressing change procedure, the medical indicia 1316,1317,1318,1319,1320,1321 set forth—from left to right—the steps of a method of changing a central catheter insertion site dressing in accordance with a predefined procedure.

In this illustrative embodiment, medical implement 1310 comprises a Chloraprep.sup.™ one-step antiseptic tool that delivers a combination of chlorhexidine gluconate and isopropyl alcohol. Medical implement 1311 comprises swabs. Medical implement 1312 comprises an impregnated disk and securement device. Medical implement 1313 comprises a ruler. Medical implement 1314 comprises a central catheter insertion site bandage covering. Medical implement 1314 comprises gauze padding. Where the medical kit (100) is configured for other medical procedures, the replacement of these implements with others will be obvious to those of ordinary skill in the art having the benefit of this disclosure.

Figure 14:
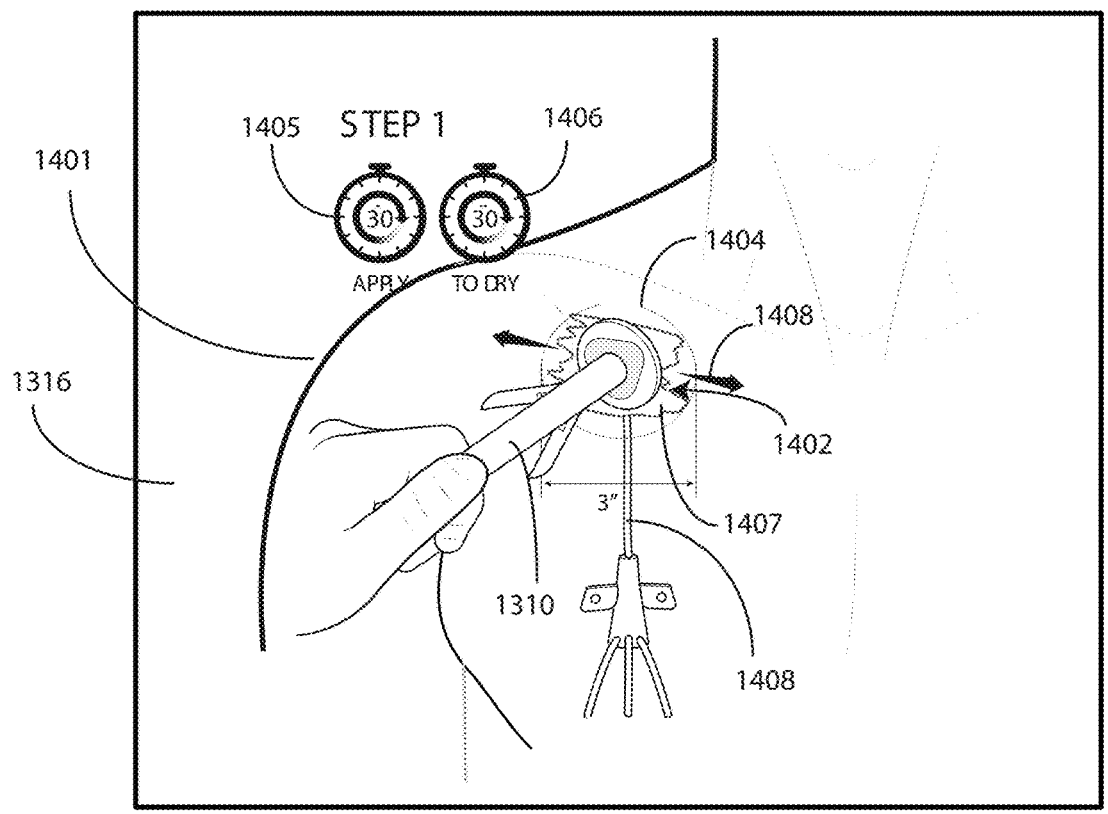
FIG. 14 illustrates explanatory instructional materials, which can be affixed to and instruct the use of, an explanatory medical kit in accordance with one or more embodiments of the disclosure.

Turning now to FIG. 14, illustrated therein is first medical indicia 1316 for using the first medical implement 1310 disposed within the first pocket (1302) of the unfolded drape (1301). In this illustrative embodiment, the first medical indicia 1316 comprise a sticker or label adhesively attached to the exterior of the first pocket (1302). In other embodiments, the first medical indicia 1316 comprise a card disposed within the first pocket (1302) that is visible from the exterior side of the first pocket (1302). Other techniques for making the first medical indicia 1316 visible from the exterior of the first pocket (1302) will be obvious to those of ordinary skill in the art having the benefit of this disclosure. As noted above, in one embodiment the first medical implement 1310 is an antiseptic cleansing tool comprising a plastic body and a sponge head that receives antiseptic 1407 from the body to be applied to the patient through the sponge head.

In this illustrative embodiment, the first medical indicia 1316 comprises an animation 1401 that instructs medical personnel to apply the first medical implement 1310 to the central catheter insertion site 1402 and to make lateral motions 1403 within an area 1404 about the central catheter insertion site 1402 to disperse the antiseptic 1407. The animation 1401 further instructs medical personnel to apply the antiseptic 1407 for at least thirty seconds, as indicated by a first duration indication 1405. The animation 1401 then instructs medical personnel to allow the antiseptic 1047 to dry for at least thirty seconds, as indicated by second duration indication 1406. Note that while this animation 1401 is for a central catheter 1408 inserted into a patient's chest, it could readily be converted for peripherally inserted central catheters by showing the patient's arm rather than the patient's chest.

Figure 15:
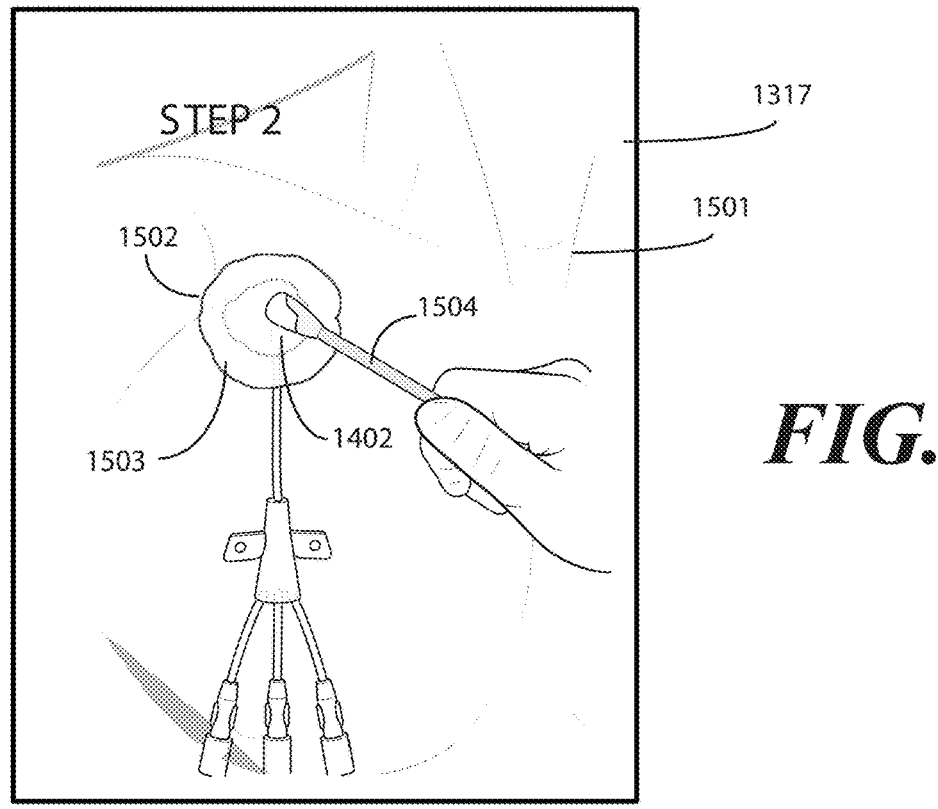
FIG. 15 illustrates explanatory instructional materials, which can be affixed to and instruct the use of, an explanatory medical kit in accordance with one or more embodiments of the disclosure.

Turning now to FIG. 15, illustrated therein is second medical indicia 1317 for using the second medical implement (1311) disposed within the second pocket (1303) of the unfolded drape (1301). As noted above, in one embodiment the second medical implement (1311) disposed within the second pocket (1303) of the unfolded drape (1301) comprises one or more swabs. In one embodiment, the one or more swabs are prewetted with an antibiotic 1502. In this illustrative embodiment, the second medical indicia 1317 comprise an animation 1501 that instructs medical personnel to apply the antibiotic 1502 from the swab 1504 to the central catheter insertion site 1402 within an area 1503 about the central catheter insertion site 1402 to disperse the antibiotic 1502.

Figure 16:
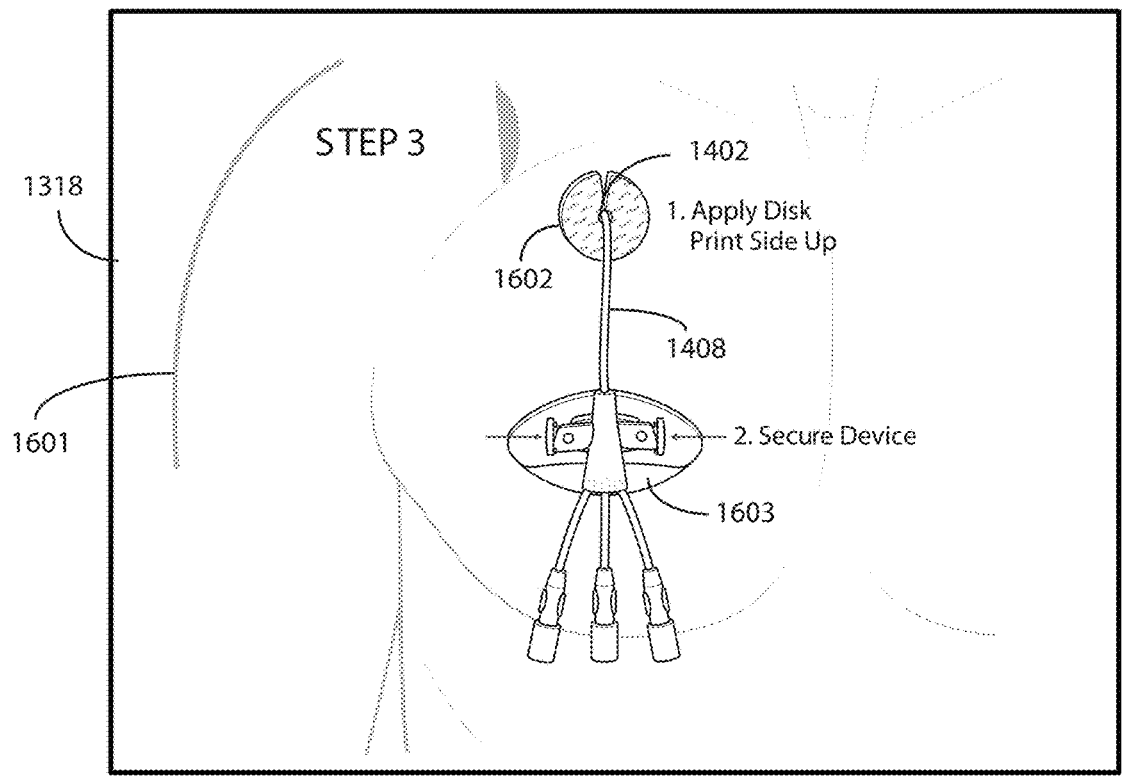
FIG. 16 illustrates explanatory instructional materials, which can be affixed to and instruct the use of, an explanatory medical kit in accordance with one or more embodiments of the disclosure.

Turning now to FIG. 16, illustrated therein is third medical indicia 1318 for using the third medical implement (1312) disposed within the third pocket (1304) of the unfolded drape (1301). In one embodiment the third medical implement (1312) disposed within the third pocket (1304) of the unfolded drape (1301) comprises two different implements: an antimicrobial impregnated disk 1602 and a central catheter line securement device 1603. In this illustrative embodiment, the third medical indicia 1318 comprise an animation 1601 that instructs medical personnel to place the antimicrobial impregnated disk 1602 about the central catheter insertion site 1402. In one embodiment, the animation 1601 instructs medical personnel to place the antimicrobial impregnated disk 1602 about the central catheter insertion site 1402 with the printed side of the antimicrobial impregnated disk 1602 facing outward to ensure that the antimicrobial impregnated disk 1602 stays affixed about the central catheter insertion site 1402. In this illustrative embodiment, the animation 1601 further instructs medical personnel to secure the central catheter 1408 to the patient's chest with the central catheter line securement device 1603.

Figure 17:
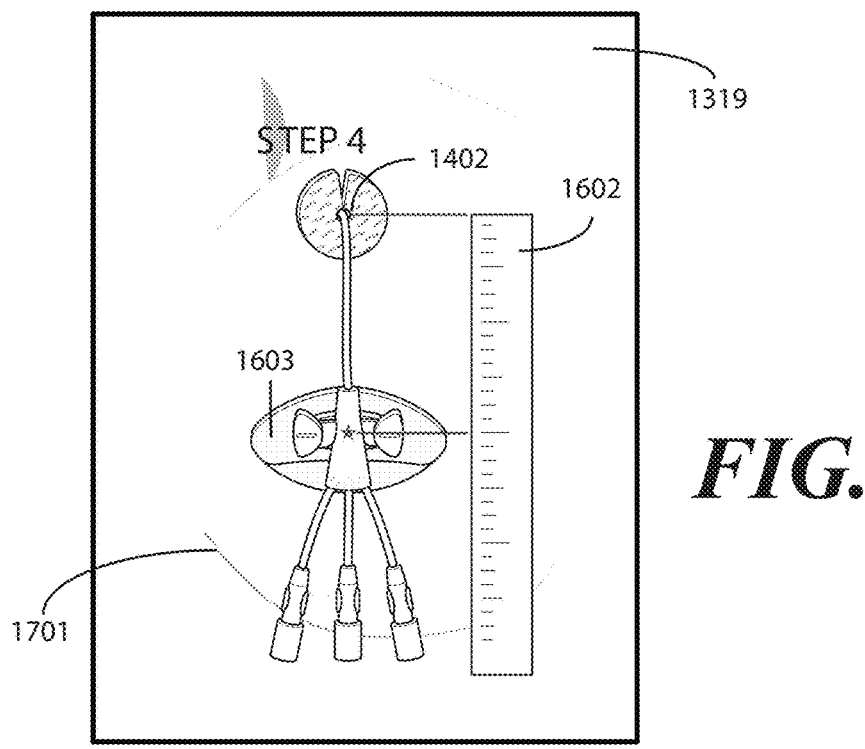
FIG. 17 illustrates explanatory instructional materials, which can be affixed to and instruct the use of, an explanatory medical kit in accordance with one or more embodiments of the disclosure.

Turning now to FIG. 17, illustrated therein is fourth medical indicia 1319 for using the fourth medical implement (1313) disposed within the fourth pocket (1305) of the unfolded drape (1301). In one embodiment the fourth medical implement (1313) comprises a ruler 1702. In this illustrative embodiment, the fourth medical indicia 1319 comprise an animation 1701 that instructs medical personnel to measure the distance between the central catheter insertion site 1402 and the central portion of the central catheter line securement device 1603 to ensure that the central catheter has not been pushed into, or pulled out of, the patient's chest.

Figure 18:
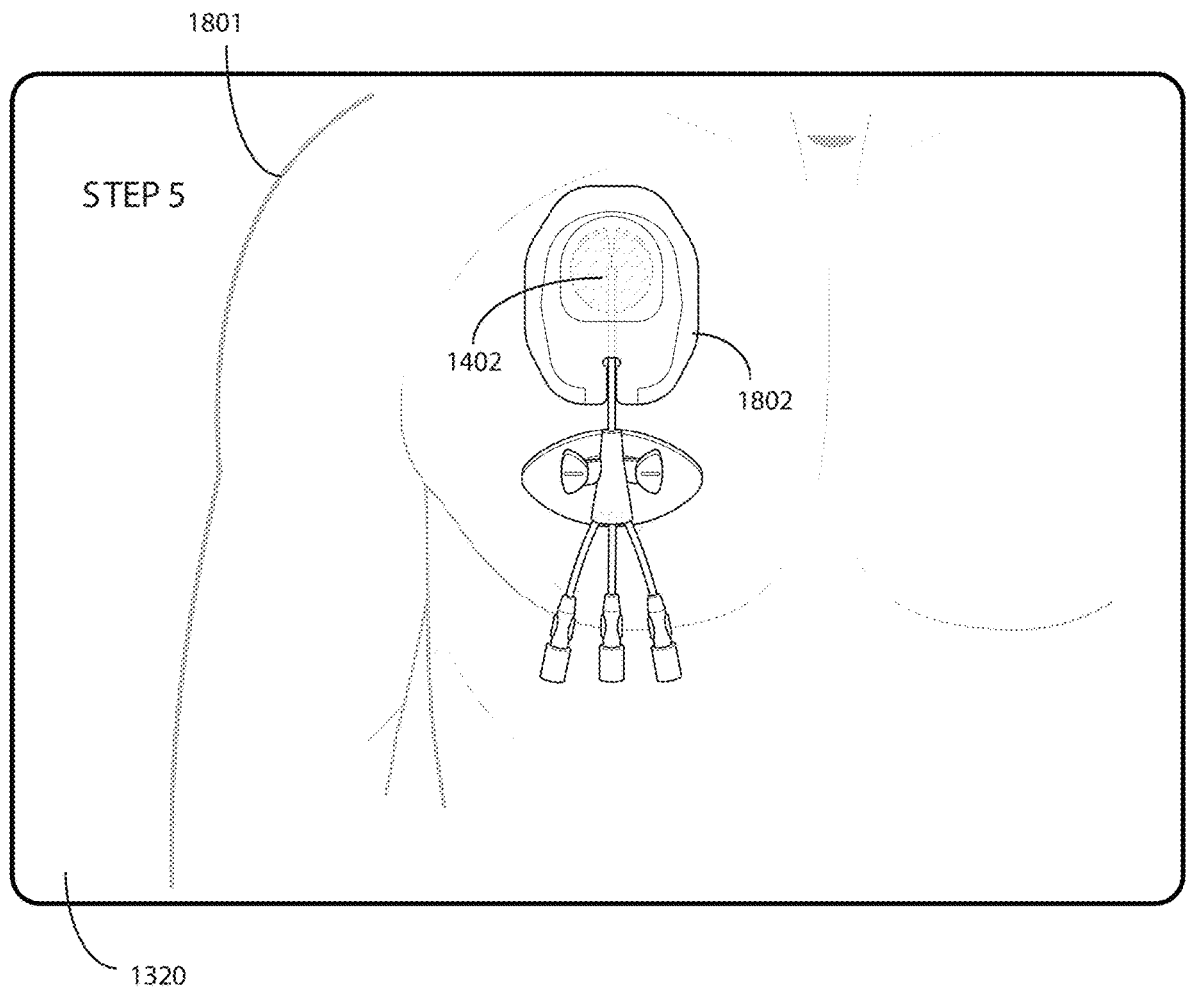
FIG. 18 illustrates explanatory instructional materials, which can be affixed to and instruct the use of, an explanatory medical kit in accordance with one or more embodiments of the disclosure.

Turning now to FIG. 18, illustrated therein is fifth medical indicia 1320 for using the fifth medical implement (1314)

disposed within the fifth pocket (1306) of the unfolded drape (1301). In one embodiment the fifth medical implement (1314) comprises a central catheter insertion site bandage covering 1802. In this illustrative embodiment, the fifth medical indicia 1320 comprise an animation 1801 that instructs medical personnel to place the central catheter insertion site bandage covering 1802 over the central catheter insertion site 1402 to complete the central catheter dressing replacement process.

It should be noted that the animations and instructions described above with reference to FIGS. 14-18 are illustrative only. Others could be substituted where the medical kit (100) is configured for a different type of procedure. Still others will be readily apparent to those of ordinary skill in the art having the benefit of this disclosure. It will be clear that these animations and instructions described above with reference to FIGS. 14-18, and the information printed thereon, can be varied in any number of ways without departing from the spirit and scope of the disclosure as described herein and recited in the following claims. For example, the number of animations and instructions described above with reference to FIGS. 14-18 can be varied. Additionally, the information printed thereon can be condensed, expanded, or altered without departing from the spirit and scope of the disclosure. Also, the exemplary information may be moved from the panels shown to other panels, as a particular application may warrant.

Figure 19:
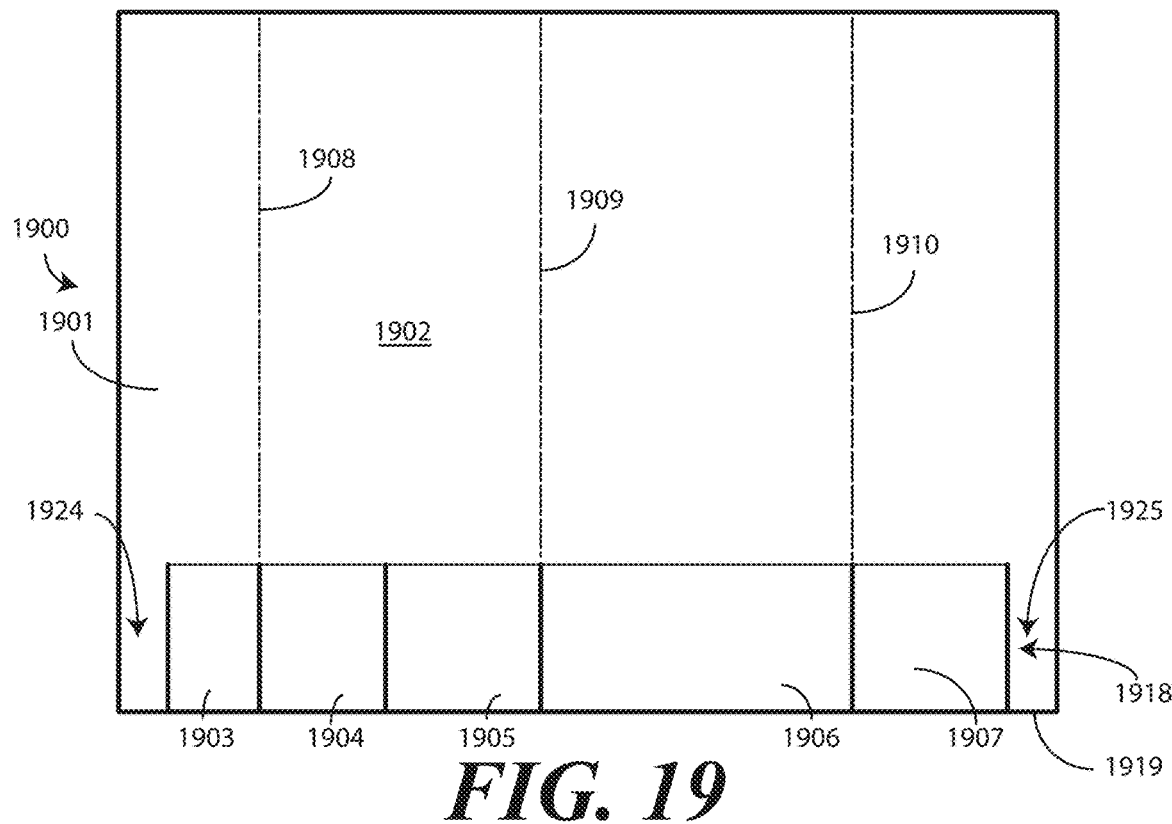
FIG. 19 illustrates a first side of an alternate unfolded drape in accordance with one or more embodiments of the disclosure.
Figure 20:
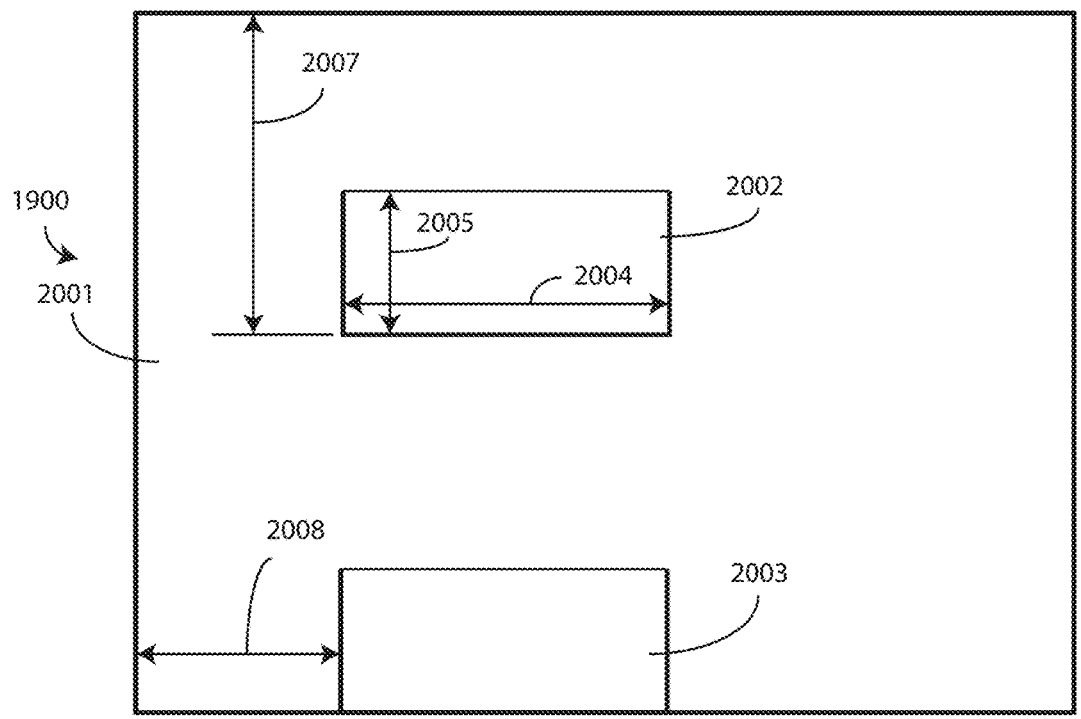
FIG. 20 illustrates a second side of an alternate unfolded drape in accordance with one or more embodiments of the disclosure.

Just as the animations an instructions described above with reference to FIGS. 14-18 can be varied and can take different forms, so too can the unfolded drape to which the animations and instructions are attached, so to can the unfolded drape. The example described above with reference to FIG. 13 was an illustrative example only. Turning now to FIGS. 19-20, illustrated therein is another unfolded drape 1900 in accordance with one or more embodiments of the disclosure. FIG. 19 illustrates a first side 1901 of the unfolded drape 1900, while FIG. 20 illustrates a second side 2001 of the unfolded drape 1900.

As shown in FIG. 19, the unfolded drape 1900 includes a layer of drape material 1902. In one embodiment, a series of pockets 1903,1904,1905,1906,1907 disposed along the layer of drape material 1902. The unfolded drape 1900 can be folded along three fold lines 1908,1909,1910 to for a folded drape as previously described.

In one embodiment, the series of pockets 1903,1904, 1905,1906,1907 is arranged in a linear, side-by-side arrangement 1918 along a bottom edge 1919 of the unfolded drape 1900. In this illustrative embodiment, additional material 1924,1925 extends beyond the sides of the series of pockets 1903,1904,1905,1906,1907 to ensure that the contents in the series of pockets 1903,1904,1905,1906,1907 remain sterile when the unfolded drape 1900 is folded. In one embodiment, the additional material 1924,1925 comprises about three centimeters of material extending beyond the first pocket 1903 and the fifth pocket 1907 as shown. As noted above, disposing each of the pockets 1903,1904,1905,1906,1907 along the base of the unfolded drape 1900 advantageously leaves a maximized, sterile work surface upon which medical personnel may work when changing a central catheter insertion site dressing.

In this illustrative embodiment, the series of pockets 1903,1904,1905,1906,1907 comprises only five pockets. This is in contrast to the six pockets described above with reference to FIG. 13. However, as shown in FIG. 20, in one embodiment the unfolded drape includes two pockets 2002, 2003 on the rear side of the unfolded drape 1900 as well. In one embodiment, rear pocket 2003 can be disposed at the exact same location as pocket 1906, but on the second side 2001 of the unfolded drape 1900. This allows a single heat sealing operation to attach both pocket 1906 and pocket 2003.

These rear side pockets 2002,2003 can be used to hold the implements described above with reference to FIGS. 7-9. Illustrating by example, implements included with the medical device cluster (702), such as the surgical mask (607), the liquid hand sanitizer (609), or the package (901) of sterile rubber gloves (610) can be placed within the pockets 2002, 2003 on the second side 2001 of the unfolded drape 1900 so that they remain in place when the folded medical drape is unfolded. For instance, the surgical mask (607) and the liquid hand sanitizer (609) could be placed in the upper pocket 2002, while the package (901) of rubber gloves (610) is placed in the lower pocket 2003. Additionally, as previously described, one or more educational prompts can be placed on the pockets 2002,2003 disposed pm the second side 2001 of the unfolded drape 1900 as well. Thus, in one embodiment first medical indicia are coupled to one or more of the pockets 2002,2003 so as to be revealed when the first upper exterior portion of a folded drape is unfolded from atop the second upper exterior portion as previously described.

In one embodiment, each of the pockets 2002,2003 has a width 2004 of about 20 centimeters so as to retain components of the medical device cluster (702). In one embodiment, the pockets 2002,2003 have a height 2005 of about nine centimeters. In this illustrative embodiment, the upper pocket 2002 has its base 2006 disposed a distance 2007 of about twenty-four centimeters from the upper side of the unfolded drape 1900. In one embodiment, each pocket 2002,2003 is disposed a distance 2008 of about thirteen centimeters from the left side of the unfolded drape 1900. In this illustrative embodiment, the unfolded drape has a width of about sixty centimeters and a height of about forty-five centimeters.

Turning back to the first side 1901 of the unfolded drape 1900, each of the series of pockets 1903,1904,1905,1906, 1907 can be configured to receive one or more medical implements as previously described. In this illustrative embodiment, medical implement (1313), i.e., the ruler, is not required. Accordingly, the number of pockets 1903,1904, 1905,1906,1907 has been reduced from six to five.

Each pocket 1903,1904,1905,1906,1907 is configured to hold a medical implement (1310, 1311,1312,1314,1315) on a one-to-one basis. In one embodiment, those medical implements (1310,1311,1312, 1314,1315) are arranged in accordance with a predefined order of use in a central catheter dressing change procedure. In other embodiments, each pocket 1903,1904,1905,1906,1907 may hold multiple medical implements. Accordingly, medical personnel can start from the left, drawing a first medical implement (1310) from the first pocket 1903, and complete a first step of the central catheter dressing change procedure. Medical personnel can then move to the second pocket 1904, draw a second medical implement (1311), and so forth, to successfully complete the central catheter dressing change procedure.

In this illustrative embodiment, the series of pockets 1903,1904,1905,1906,1907 are formed and defined by thermally bonding a clear plastic film to the unfolded drape 1900. As noted above, other techniques for bonding the series of pockets 1903,1904,1905,1906,1907 to the unfolded drape 1900 will be obvious to those of ordinary skill in the art having the benefit of this disclosure.

It should be noted that the sizes and widths of the series of pockets 1903,1904,1905,1906, 1907 can be varied as well. For example, in this illustrative embodiment the first pocket 1903 is six centimeters wide, while the second pocket 1904 is eight centimeters wide. The third pocket 1905 is ten centimeters wide, as is the fifth pocket 1906. In this illustrative embodiment, the fourth pocket 1906 is twenty centimeters wide. Each pocket 1903,1904,1905,1906,1907 is nine centimeters deep. Other widths and extents of the series of pockets 1903,1904,1905,1906,1907 will be obvious to those of ordinary skill in the art having the benefit of this disclosure.

In one embodiment, each pocket 1903,1904,1905,1906, 1907 has medical indicia (1316,1317,1318,1320,1321) attached thereto. The medical indicia (1316,1317,1318, 1320,1321) can each comprise one or more educational prompts (described above with reference to FIGS. 14-18) that instruct medical personnel regarding how to use a particular medical implement disposed in a pocket to which the medical indicia is attached. Illustrating by example, medical indicia (1316), which can be attached to pocket 1903, can comprise an educational prompt that instructs medical personnel regarding how to use medical implement (1310), which can be stowed in pocket 1903. Similarly, medical indicia (1317), which can be attached to pocket 1904, can comprise one or more educational prompts instructing medical personnel how to use medical implement (1311), and so forth.

Figure 21:
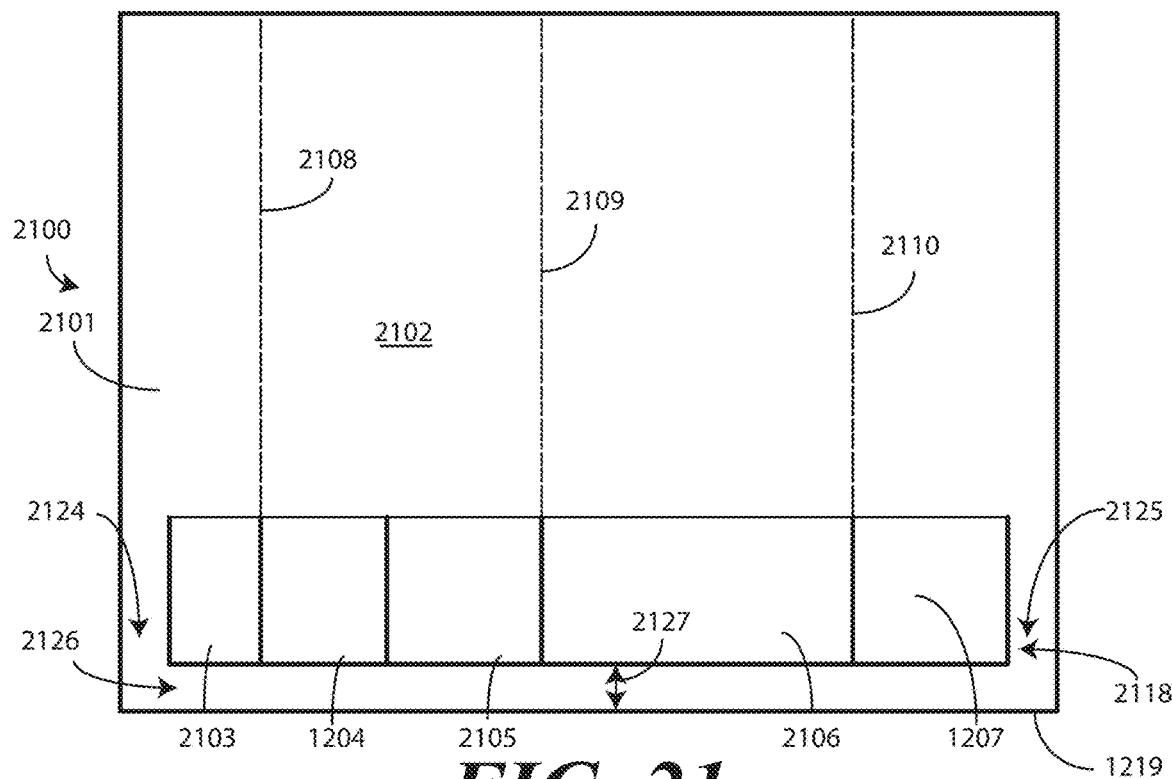
FIG. 21 illustrates a first side of yet another unfolded drape in accordance with one or more embodiments of the disclosure.
Figure 22:
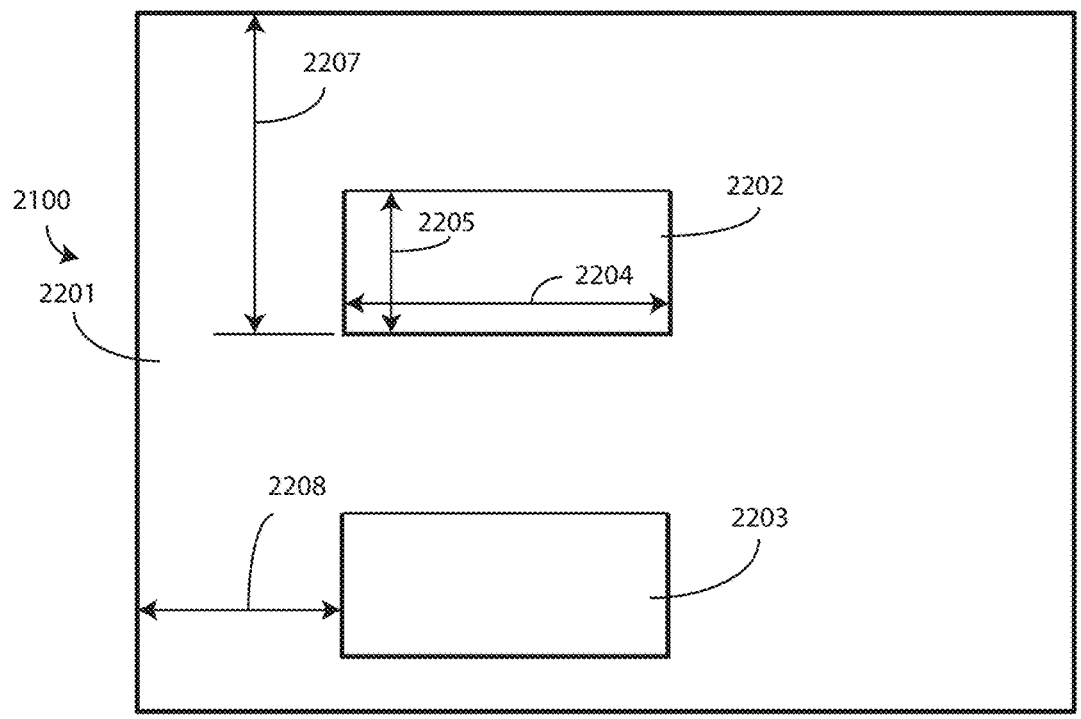
FIG. 22 illustrates a second side of yet another unfolded drape in accordance with one or more embodiments of the disclosure.

Turning now to FIGS. 21-22, illustrated therein is yet another unfolded drape 2100 in accordance with one or more embodiments of the disclosure. FIG. 21 illustrates a first side 2101 of the unfolded drape 2100, while FIG. 22 illustrates a second side 2201 of the unfolded drape 2100. The unfolded drape 2200 of FIGS. 21 and 22 is similar to that of FIGS. 19-20. However, rather than having pockets 2103,2104, 2105,2106,2107 disposed along a lower edge 2119, there is a separation area 2126 between the pockets 2103,2104,2105, 2106,2107 and the lower edge 2119 of about three centimeters.

As shown in FIG. 21, the unfolded drape 2100 includes a layer of drape material 2102. In one embodiment, a series of pockets 2103,2104,2105,2106,2107 disposed along the layer of drape material 2102. The unfolded drape 2100 can be folded along three fold lines 2108,2109,2110 to for a folded drape as previously described.

In one embodiment, the series of pockets 2103,2104, 2105,2106,2107 is arranged in a linear, side-by-side arrangement 2118, separated from a bottom edge 2119 of the unfolded drape 2100 by a distance 2127 of about three centimeters. In this illustrative embodiment, additional material 2124,2125 also extends beyond the sides of the series of pockets 2103,2104,2105,2106,2107 to ensure that the contents in the series of pockets 2103,2104,2105,2106, 2107 remain sterile when the unfolded drape 2100 is folded. In one embodiment, the additional material 2124,2125 comprises about three centimeters of material extending beyond the first pocket 2103 and the fifth pocket 2107 as shown. As noted above, disposing each of the pockets 2103,2104,2105, 2106,2107 along the base of the unfolded drape 1900 advantageously leaves a maximized, sterile work surface upon which medical personnel may work when changing a central catheter insertion site dressing.

In this illustrative embodiment, the series of pockets 2103,2104,2105,2106,2107 comprises five pockets. As shown in FIG. 22, in one embodiment the unfolded drape includes two pockets 2202,2203 on the rear side of the unfolded drape 2100 as well. In one embodiment, rear pocket 2203 can be disposed at the exact same location as pocket 2106, but on the second side 2201 of the unfolded drape 2100. This allows a single heat-sealing operation to attach both pocket 2106 and pocket 2203.

These rear side pockets 2202,2203 can be used to hold the implements described above with reference to FIGS. 7-9. Illustrating by example, implements included with the medical device cluster (702), such as the surgical mask (607), the liquid hand sanitizer (609), or the package (901) of sterile rubber gloves (610) can be placed within the pockets 2202, 2203 on the second side 2201 of the unfolded drape 2100 so that they remain in place when the folded medical drape is unfolded. For instance, the surgical mask (607) and the liquid hand sanitizer (609) could be placed in the upper pocket 2202, while the package (901) of rubber gloves (610) is placed in the lower pocket 2203. Additionally, as previously described, one or more educational prompts can be placed on the pockets 2202,2203 disposed pm the second side 2201 of the unfolded drape 2100 as well. Thus, in one embodiment first medical indicia are coupled to one or more of the pockets 2202,2203 so as to be revealed when the first upper exterior portion of a folded drape is unfolded from atop the second upper exterior portion as previously described.

In one embodiment, each of the pockets 2202,2203 has a width 2204 of about twenty centimeters so as to retain components of the medical device cluster (702). In one embodiment, the pockets 2202,2203 have a height 2205 of about nine centimeters. In this illustrative embodiment, the upper pocket 2202 has its base 2206 disposed a distance 2207 of about twenty-four centimeters from the upper side of the unfolded drape 2100. In one embodiment, each pocket 2202,2203 is disposed a distance 2208 of about thirteen centimeters from the left side of the unfolded drape 2100. In this illustrative embodiment, the unfolded drape has a width of about sixty-two centimeters and a height of about forty-five centimeters.

Turning back to the first side 2101 of the unfolded drape 2100, each of the series of pockets 2103,2104,2105,2106, 2107 can be configured to receive one or more medical implements as previously described. In this illustrative embodiment, medical implement (1313), i.e., the ruler, is not required. Accordingly, the number of pockets 2103,2104, 2105,2106,2107 has been reduced from six to five.

Each pocket 2103,2104,2105,2106,2107 is configured to hold a medical implement (1310, 1311,1312,1314,1315) on a one-to-one basis. In one embodiment, those medical implements (1310,1311,1312, 1314,1315) are arranged in accordance with a predefined order of use in a central catheter dressing change procedure. In other embodiments, each pocket 2103,2104,2105,2106,2107 may hold multiple medical implements. Accordingly, medical personnel can start from the left, drawing a first medical implement (1310) from the first pocket 2103, and complete a first step of the central catheter dressing change procedure. Medical personnel can then move to the second pocket 2104, draw a second medical implement (1311), and so forth, to successfully complete the central catheter dressing change procedure.

In this illustrative embodiment, the series of pockets 2103,2104,2105,2106,2107 are formed and defined by thermally bonding a clear plastic film to the unfolded drape 2100. As noted above, other techniques for bonding the series of pockets 2103,2104,2105,2106,2107 to the unfolded drape 2100 will be obvious to those of ordinary skill in the art having the benefit of this disclosure.

It should be noted that the sizes and widths of the series of pockets 2103,2104,2105,2106, 2107 can be varied as well. For example, in this illustrative embodiment the first pocket 2103 is six centimeters wide, while the second pocket 12104 is ten centimeters wide. The third pocket 2105 is ten centimeters wide, as is the fifth pocket 2106. In this illustrative embodiment, the fourth pocket 2106 is twenty centimeters wide. Each pocket 2103,2104,2105,2106,2107 is nine centimeters deep. Other widths and extents of the series of pockets 2103,2104,2105,2106,2107 will be obvious to those of ordinary skill in the art having the benefit of this disclosure.

In one embodiment, each pocket 2103,2104,2105,2106, 2107 has medical indicia (1316,1317,1318,1320,1321) attached thereto. The medical indicia (1316,1317,1318, 1320,1321) can each comprise one or more educational prompts (described above with reference to FIGS. 14-18) that instruct medical personnel regarding how to use a particular medical implement disposed in a pocket to which the medical indicia is attached. Illustrating by example, medical indicia (1316), which can be attached to pocket 2103, can comprise an educational prompt that instructs medical personnel regarding how to use medical implement (1310), which can be stowed in pocket 1903. Similarly, medical indicia (1317), which can be attached to pocket 2104, can comprise one or more educational prompts instructing medical personnel how to use medical implement (1311), and so forth.

Figure 23:
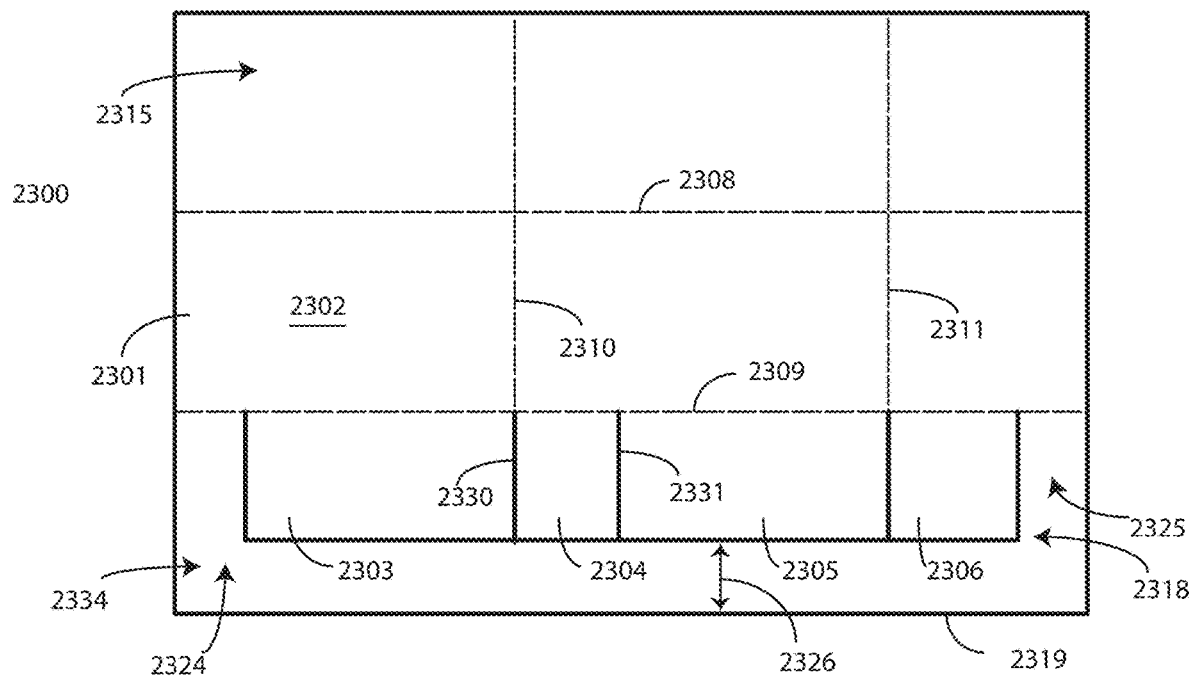
FIG. 23 illustrates a first side of yet another unfolded drape in accordance with one or more embodiments of the disclosure.
Figure 24:
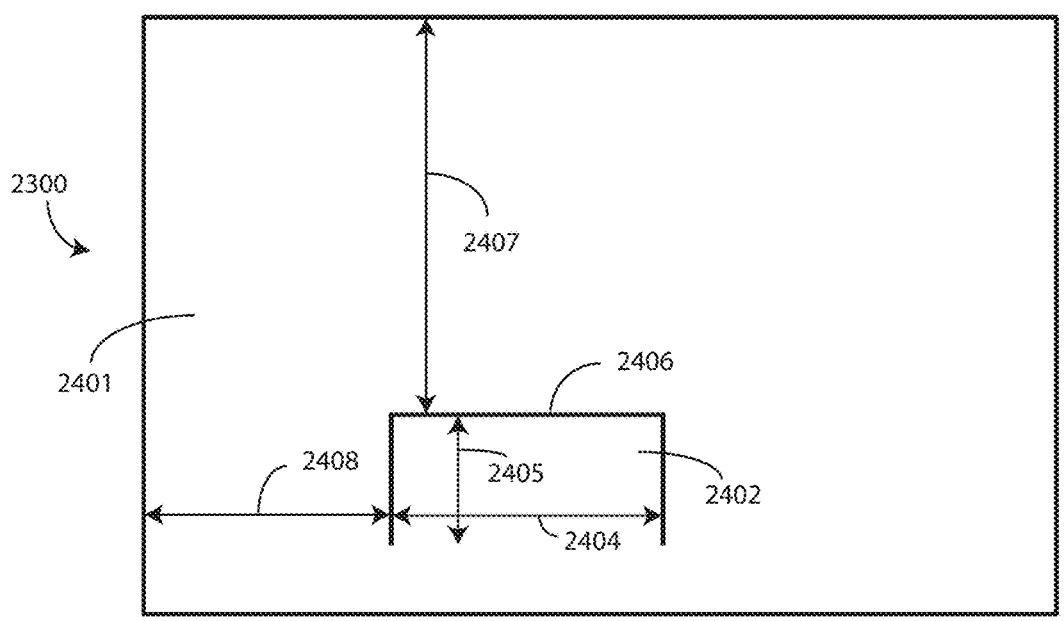
FIG. 24 illustrates a second side of yet another unfolded drape in accordance with one or more embodiments of the disclosure.

Turning now to FIGS. 23-24, illustrated therein is yet another unfolded drape 2300 in accordance with one or more embodiments of the disclosure. FIG. 23 illustrates a first side 2301 of the unfolded drape 2300, while FIG. 24 illustrates a second side 2401 of the unfolded drape 2400. The unfolded drape 2400 of FIGS. 23 and 24 is somewhat similar to that of FIGS. 21-22. However, rather than having five pockets (2103,2104,2105,2106,2107), the unfolded drape 2300 of FIGS. 23-24 includes four pockets 2303,2304,2305,2306. As with the embodiment of FIGS. 21-22, the four pockets 2303,2304,2305,2306 are disposed a predefined distance 2326 from a bottom edge 2319 of the unfolded drape 2300. In one embodiment, the predefined distance 2326 is about five centimeters, plus or minus 0.5 centimeters.

As shown in FIG. 23, the unfolded drape 2300 includes a layer of drape material 2302. In one embodiment, the layer of drape material 2302 is about sixty-four centimeters wide and about forty-two centimeters tall.

In one embodiment, the four pockets 2303,2304,2305, 2306 are thermally bonded with a heat seal to, and along, the layer of drape material 2302. In this illustrative embodiment, the unfolded drape 2300 includes four fold lines: a first fold line 2308, a second fold line 2309, a third fold line 2310, and a fourth fold line 2311. In this illustrative embodiment, the first fold line 2308 and the second fold line 2309 are parallel to each other, and are substantially orthogonal or perpendicular to the third fold line 2310 and the fourth fold line 2311, respectively. Similarly, in this illustrative embodiment, the third fold line 2311 and the fourth fold line 2311 are parallel to each other, and are substantially orthogonal or perpendicular to the first fold line 2308 and the second fold line 2309.

In one embodiment, the four pockets 2303,2304,2305, 2306 are arranged in a linear, side-by-side arrangement 2318, separated from a bottom edge 2319 of the unfolded drape 2300 by a predefined distance 2326 of about five centimeters. In one embodiment, the four pockets 2303, 2304,2305,2306 are arranged such that each pocket abuts at least one adjacent pocket at a common border. Illustrating by example, pocket 2303 abuts pocket 2304 at common border 2330, while pocket 2304 abuts pocket 2305 at common border 2331, and so forth. In this illustrative embodiment, the third fold line 2310 and the fourth fold line 2311 are substantially parallel with the common borders 2330,2331 between adjacent pockets, while the first fold line 2308 and the second fold lien 2309 are substantially perpendicular with the common borders 2330,2331. Additionally, in this illustrative embodiment the third fold line 2310 is collinear with common border 2330, while the fourth fold line 2311 is collinear with common border 2332.

In one or more embodiments, some of the four pockets 2303,2304,2305,2306 are wider than others. For example, in this illustrative embodiment, pocket 2303 and pocket 2305 are wider than are pocket 2304 and pocket 2306. In one embodiment, pocket 2303 and pocket 2305 are about nineteen centimeters wide, while pocket 2304 is about seven centimeters wide and pocket 2306 is about nine centimeters wide. Accordingly, in this embodiment two pockets 2303, 2305 of the four pockets 2303,2304,2305,2306 are wider than two other pockets 2304,2306 of the four pockets 2303,2304,2305,2306. In one embodiment, each of the four pockets 2303,2304,2305,2306 is about nine centimeters deep. In this illustrative embodiment, the four pockets 2303,2304,2305,2306 are manufactured from a clear plastic film that is thermally bonded to the unfolded drape 2300.

In one or more embodiments, the unfolded drape 2300 extends, in all directions, beyond a perimeter 2333 of the four pockets 2303,2304,2305,2306. In this illustrative embodiment, additional material 2324,2325 extends beyond the sides of the four pockets 2303,2304,2305,2306 to ensure that the contents in the four pockets 2303,2304,2305,2306 remain sterile when the unfolded drape 2300 is folded. Similarly, additional material 2135 extends beyond the bottom of the four pockets 2303,2304,2305,2306, while additional material 2135 extends beyond the top of the four pockets 2303,2304,2305,2306. This extension in four directions from the four pockets 2303,2304,2305,2306 results in an extension in all directions from the perimeter 2333 of the four pockets 2303,2304,2305,2306. In one embodiment, the additional material 2124,2125 comprises about five centimeters of material extending beyond pocket 2303 and the pocket 2306 as shown.

As shown in FIG. 24, in one embodiment the unfolded drape 2300 includes one pocket 2402 on the rear side of the unfolded drape 2300 as well. In one embodiment, the pocket 2402 on the rear side has a width 2404 of about nineteen centimeters and a depth 2405 of about nine centimeters.

As shown in FIG. 24, in this illustrative embodiment the pocket 2402 disposed on the rear side of the unfolded drape 2300 is rotated 180 degrees relative to the four pockets 2303,2304,2305,2306 disposed on the front of the unfolded drape 2300. Said differently, as viewed in FIG. 23, each of the four pockets 2303,2304,2305,2306 opens up. By contrast, as viewed in FIG. 24, the pocket 2402 disposed on the rear side of the unfolded drape 2300 opens down.

In one or more embodiments, the pocket 2402 disposed on the rear side of the unfolded drape 2300 can be used to hold one or more of the implements described above with reference to FIGS. 7-9. Illustrating by example, implements included with the medical device cluster (702), such as the surgical mask (607), the liquid hand sanitizer (609), or the package (901) of sterile rubber gloves (610) can be placed within the pocket 2402 on the second side 2301 of the unfolded drape 2300 so that they remain in place when the folded medical drape is unfolded. For instance, the surgical mask (607) and the liquid hand sanitizer (609) could be placed in the pocket 2402. Alternatively, the package (901) of rubber gloves (610) can placed in the pocket 2402. Additionally, as previously described, one or more educational prompts can be placed on the pocket 2402 disposed on the second side 2401 of the unfolded drape 2300 as well. Thus, in one embodiment first medical indicia are coupled to the pocket 2402 so as to be revealed when the drape is unfolded.

In this illustrative embodiment, the pocket 2402 has its base 2406 disposed a distance 2407 of about twenty-eight centimeters from the upper side of the unfolded drape 2300. In one embodiment, the pocket 2402 is disposed a distance 2408 of about 17.5 centimeters from the left side of the unfolded drape 2300.

Turning back to the first side 2301 of the unfolded drape 2300, each of the four pockets 2303,2304,2305,2306 can be configured to receive one or more medical implements as previously described. In this illustrative embodiment, neither medical implement (1313), i.e., the ruler, nor medical implement (1315), i.e., the extra items, is required. Accordingly, the number of pockets has been reduced from six to four.

In one or more embodiments, each pocket of the four pockets 2303,2304,2305,2306 is configured to hold a medical implement (1310, 1311,1312,1314) on a one-to-one basis. In other embodiments, each pocket of the four pockets 2303,2304,2305,2306 is configured to hold more than one medical implement (1310, 1311,1312,1314). In one embodiment, those medical implements (1310,1311,1312, 1314) are arranged in accordance with a predefined order of use in a central catheter dressing change procedure. In another embodiment, those medical implements (1310,1311,1312, 1314) are arranged in accordance with a predefined order of use in a peripheral intravenous catheter insertion site dressing change procedure. In other embodiments, each pocket of the four pockets 2303,2304,2305,2306 may hold multiple medical implements. Accordingly, medical personnel can start from the left, drawing a first medical implement (1310) from the first pocket 2303, and complete a first step of the central catheter dressing change procedure, the intravenous catheter insertion site dressing change procedure, or other procedure. Medical personnel can then move to the second pocket 2304, draw a second medical implement (1311), and so forth, to successfully complete the central catheter dressing change procedure, the intravenous catheter insertion site dressing change procedure, or other procedure.

In this illustrative embodiment, the four pockets 2303, 2304,2305,2306 are formed and defined by thermally bonding a clear plastic film to the unfolded drape 2300. As noted above, other techniques for bonding the four pockets 2303, 2304,2305,2306 and the other pocket 2402 to the unfolded drape 2300 will be obvious to those of ordinary skill in the art having the benefit of this disclosure. It should be noted that the sizes and widths of the four pockets 2303,2304, 2305,2306 can be varied as well.

In one embodiment, each pocket of the four pockets 2303,2304,2305,2306 has medical indicia (1316,1317,1318, 1320) attached thereto. The medical indicia (1316,1317, 1318,1320) can each comprise one or more educational prompts (described above with reference to FIGS. 14-18) that instruct medical personnel regarding how to use a particular medical implement disposed in a pocket to which the medical indicia is attached. Illustrating by example, medical indicia (1316), which can be attached to pocket 2303, can comprise an educational prompt that instructs medical personnel regarding how to use medical implement (1310), which can be stowed in pocket 2303. Similarly, medical indicia (1317), which can be attached to pocket 2304, can comprise one or more educational prompts instructing medical personnel how to use medical implement (1311), and so forth.

Turning now to FIGS. 25-28, illustrated therein are one or more method steps for folding the unfolded drape (2300) to form a folded drape 2800. Beginning with FIG. 25, a first portion 2501 of the unfolded drape 2300 is folded with a book fold 2502 about the fourth fold line 2311 to form a partially folded drape 2500. In FIG. 26, a second portion 2601 of the unfolded drape (2300) is folded with a second book fold 2602 about the third fold line 2310, toward the first portion 2501 of the partially folded drape (2500) to form another partially folded drape 2600.

Turning to FIG. 27, a third portion 2701 of the unfolded drape 2300 is folded with third book fold 2702 along the first fold line 2309 toward the top of the partially folded drape (2600). When this occurs, it inverts the four pockets (2303, 2304,2305,2306). Additionally, it inverts the pocket 2402 disposed on the second side of the drape, making it accessible. Once this is done, as shown in FIG. 28, a fourth portion 2801 of the unfolded drape (2300) is folded with a fourth book fold 2802 about the second fold line 2308 to cause the fourth portion 2801 of the unfolded drape (2300) to cover the inverted four pockets (2303,2304,2305,2306). This results in a folded drape 2800.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A medical kit, comprising:
   a drape;
   a plurality of pockets disposed a predefined distance from a bottom edge of a first side of the drape in a linear, side-by-side arrangement, wherein each pocket of the plurality of pockets abuts at least one adjacent pocket at a common border;
   a plurality of medical implements, stowed in the plurality of pockets;
   one or more other pockets disposed along a second side of the drape, wherein the one or more other pockets are rotated 180 degrees relative to the each pocket of the plurality of pockets; and
   medical indicia disposed along each pocket of the plurality of pockets, the medical indicia comprising one or more educational prompts that instruct medical personnel how to use a particular medical implement disposed in a pocket to complete a central catheter dressing change.

2. The medical kit of claim 1, the medical indicia comprising an animation.

3. The medical kit of claim 2, the animation instructing the medical personnel to apply at least one medical implement to a central catheter insertion site.

4. The medical kit of claim 1, the drape folded with a first book fold along a first fold line and a second book fold along a second fold line to define a partially folded drape, wherein the first fold line and the second fold line are parallel with the common border.

5. The medical kit of claim 4, the drape further folded with a third book fold along a third fold line that is orthogonal with both the first fold line and the second fold line, wherein the third book fold inverts the plurality of pockets.

6. The medical kit of claim 5, the drape further folded with a fourth book fold along a fourth fold line that is parallel with third fold line, wherein the fourth book fold causes a portion of the drape to cover the plurality of pockets, which have been inverted by the third book fold.

7. The medical kit of claim 6, further comprising one or more of a surgical mask, liquid hand sanitizer, gloves, or combinations thereof disposed in the one or more other pockets.

8. The medical kit of claim 7, further comprising first medical indicia coupled to the one or more other pockets so as to be revealed when the first upper exterior portion of the folded drape is unfolded from atop the second upper exterior portion.

9. The medical kit of claim 7, the first medical indicia instructing the medical personnel to one or more of don the surgical mask, apply the liquid hand sanitizer, don the gloves, or combinations thereof.

10. The medical kit of claim 6, wherein the plurality of pockets comprises only four pockets.

11. The medical kit of claim 10, wherein the drape extends, in all directions, beyond a perimeter of the plurality of pockets.

12. The medical kit of claim 11, wherein two pockets of the plurality of pockets are wider than two other pockets of the plurality of pockets.

13. The medical kit of claim 12, the drape sealed within a wrap keeping the drape sterile.

14. The medical kit of claim 12, the plurality of pockets manufactured from a clear plastic film thermally bonded to the drape.

15. The medical kit of claim 14, the one or more other pockets comprising a single pocket.

16. A medical kit, comprising:
a drape; and
four pockets disposed along, and separated from, an edge of a first side of the the drape, wherein each pocket of the four pockets abuts at least one adjacent pocket at a common border;
at least one pocket disposed along a second side of the drape, wherein the at least one pocket is rotated 180 degrees relative to each of the four pockets;
wherein:
the drape is folded about a first fold line and a second fold line,
wherein the first fold line and the second fold line are parallel to the common border; and
thereafter, the drape is folded about a third fold line that is perpendicular to the first fold line and the second fold line to invert the four pockets; and
thereafter, the drape is folded about a fourth fold line to cover the four pockets, inverted by folding about the third fold line, with a portion of the drape.

17. The medical kit of claim 16, further comprising one or more of a surgical mask, liquid hand sanitizer, gloves, or combinations thereof, each being is disposed a pocket.

18. The medical kit of claim 16, the four pockets arranged in a linear, side-by-side arrangement, the four pockets having medical indicia disposed thereon, the medical indicia comprising one or more educational prompts that instruct medical personnel how to use a particular medical implement of the medical kit.

19. The medical kit of claim 18, further comprising patient instructional material.

20. The medical kit of claim 18, the drape sealed within a wrap.

* * * * *